(12) United States Patent
Tsuchiya et al.

(10) Patent No.: US 6,610,485 B1
(45) Date of Patent: Aug. 26, 2003

(54) METHODS FOR ISOLATING A CDNA ENCODING A MEMBRANE-BOUND PROTEIN

(75) Inventors: Masayuki Tsuchiya, Gotemba (JP); Mikiyoshi Saito, Gotemba (JP); Toshihiko Ohtomo, Gotemba (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/700,820

(22) PCT Filed: Apr. 30, 1999

(86) PCT No.: PCT/JP99/02341
§ 371 (c)(1),
(2), (4) Date: May 2, 2001

(87) PCT Pub. No.: WO99/60113
PCT Pub. Date: Nov. 25, 1999

(30) Foreign Application Priority Data

May 20, 1998 (JP) ............................................. 10/138652
Oct. 1, 1998 (JP) ............................................. 10/279876

(51) Int. Cl.[7] ........................... C12Q 1/68; C12P 21/04
(52) U.S. Cl. .......................................... 435/6; 435/69.7
(58) Field of Search ........................... 435/6, 810, 69.7

(56) References Cited

U.S. PATENT DOCUMENTS 5,468,614 A * 11/1995 Fields et al. ................... 435/6
5,525,486 A   6/1996 Honjo et al. ................ 435/69.1

FOREIGN PATENT DOCUMENTS

| JP | 11-32779 | 9/1999 |
| WO | WO 96/40904 | 12/1996 |
| WO | WO 98/03645 | 1/1998 |

OTHER PUBLICATIONS

Kojima et al., "A signal sequence trap based on a constitutively active cytokine receptor", Nature Biotech., 17:487–490, 1999.
Tashiro et al., "Signal Sequence Trap: A Cloning Strategy for Secreted Proteins and Type I Membrane Proteins", Science, 261:600–603, 1993.
Kelley, et al., "Functional Significance and Evolutionary Development of the 5'–Terminal Regions of Immunoglobulin Variable–Region Genes", Cell, vol. 29(2), pp. 681–689 (1992).
Thibault, et al., "Characterization and Biologic Activities of Recombinant Rat Soluble Interleukin–6 Receptor", Journal of Interferon and Cytokine Research, vol. 16(11), pp. 973–981 (1996).
Lord, et al., "Leukemia Inhibitory Factor and Interleukin–6 Trigger the Same Immediate Early Response, Including Tyrosine Phosphorylation, upon Induction of Myeloid Leukemia Differention", Molecular and Cellular Biology, vol. 11(9), pp. 4371–4379 (1991).

* cited by examiner

*Primary Examiner*—Kenneth R. Horlick
(74) *Attorney, Agent, or Firm*—Fish & Richardson P.C.

(57) ABSTRACT

A method and kit are provided for selectively isolating genes encoding membrane-bound proteins by fusing proteins to a secretable protein having a binding affinity to an antigen (e.g., an antibody), expressing these fusions in host cells, and selectively isolating individual host cells by their ability to bind the antigen via the fusion protein. Host cells expressing fusion proteins that do not contain a membrane binding domain will be relatively unable to bind the antigen, since the fusion proteins in those cells are secreted and unattached to their host cells. The method and kit disclosed herein are particularly useful for identifying genes for membrane-bound proteins represented in cDNA libraries.

13 Claims, 7 Drawing Sheets

FIG. 6

SEQUENCE LISTING

```
<160> NUMBER OF SEQ ID NOS: 39

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence:Peptide
      Linker Sequence
<400> SEQUENCE: 1

Gly Gly Gly Gly Ser Gly Gly Gly Gly Ser Gly Gly Gly Gly Ser
 1               5                  10                  15

<210> SEQ ID NO 2
<211> LENGTH: 1035
<212> TYPE: DNA
<213> ORGANISM: Homo sapiens
<220> FEATURE:
<221> NAME/KEY: CDS
<222> LOCATION: (1)..(1035)

<400> SEQUENCE: 2 atg ctg gcc gtc ggc tgc gcg ctg ctg gct gcc ctg ctg gcc gcg ccg      48
Met Leu Ala Val Gly Cys Ala Leu Leu Ala Ala Leu Leu Ala Ala Pro
 1               5                  10                  15 gga gcg gcg ctg gcc cca agg cgc tgc cct gcg cag gag gtg gca aga      96
Gly Ala Ala Leu Ala Pro Arg Arg Cys Pro Ala Gln Glu Val Ala Arg
                20                  25                  30 ggc gtg ctg acc agt ctg cca gga gac agc gtg act ctg acc tgc ccg     144
Gly Val Leu Thr Ser Leu Pro Gly Asp Ser Val Thr Leu Thr Cys Pro
            35                  40                  45 ggg gta gag ccg gaa gac aat gcc act gtt cac tgg gtg ctc agg aag     192
Gly Val Glu Pro Glu Asp Asn Ala Thr Val His Trp Val Leu Arg Lys
        50                  55                  60 ccg gct gca ggc tcc cac ccc agc aga tgg gct ggc atg gga agg agg     240
Pro Ala Ala Gly Ser His Pro Ser Arg Trp Ala Gly Met Gly Arg Arg
    65                  70                  75                  80 ctg ctg ctg agg tcg gtg cag ctc cac gac tct gga aac tat tca tgc     288
Leu Leu Leu Arg Ser Val Gln Leu His Asp Ser Gly Asn Tyr Ser Cys
                85                  90                  95
```

```
tac cgg gcc ggc cgc cca gct ggg act gtg cac ttg ctg gtg gat gtt    336
Tyr Arg Ala Gly Arg Pro Ala Gly Thr Val His Leu Leu Val Asp Val
            100                 105                 110 ccc ccc gag gag ccc cag ctc tcc tgc ttc cgg aag agc ccc ctc agc    384
Pro Pro Glu Glu Pro Gln Leu Ser Cys Phe Arg Lys Ser Pro Leu Ser
        115                 120                 125 aat gtt gtt tgt gag tgg ggt cct cgg agc acc cca tcc ctg acg aca    432
Asn Val Val Cys Glu Trp Gly Pro Arg Ser Thr Pro Ser Leu Thr Thr
130                 135                 140 aag gct gtg ctc ttg gtg agg aag ttt cag aac agt ccg gcc gaa gac    480
Lys Ala Val Leu Leu Val Arg Lys Phe Gln Asn Ser Pro Ala Glu Asp
145                 150                 155                 160 ttc cag gag ccg tgc cag tat tcc cag gag tcc cag aag ttc tcc tgc    528
Phe Gln Glu Pro Cys Gln Tyr Ser Gln Glu Ser Gln Lys Phe Ser Cys
                165                 170                 175 cag tta gca gtc ccg gag gga gac agc tct ttc tac ata gtg tcc atg    576
Gln Leu Ala Val Pro Glu Gly Asp Ser Ser Phe Tyr Ile Val Ser Met
            180                 185                 190 tgc gtc gcc agt agt gtc ggg agc aag ttc agc aaa act caa acc ttt    624
Cys Val Ala Ser Ser Val Gly Ser Lys Phe Ser Lys Thr Gln Thr Phe
        195                 200                 205 cag ggt tgt gga atc ttg cag cct gat ccg cct gcc aac atc aca gtc    672
Gln Gly Cys Gly Ile Leu Gln Pro Asp Pro Pro Ala Asn Ile Thr Val
210                 215                 220 act gcc gtg gcc aga aac ccc cgc tgg ctc agt gtc acc tgg caa gac    720
Thr Ala Val Ala Arg Asn Pro Arg Trp Leu Ser Val Thr Trp Gln Asp
225                 230                 235                 240 ccc cac tcc tgg aac tca tct ttc tac aga cta cgg ttt gag ctc aga    768
Pro His Ser Trp Asn Ser Ser Phe Tyr Arg Leu Arg Phe Glu Leu Arg
                245                 250                 255 tat cgg gct gaa cgg tca aag aca ttc aca aca tgg atg gtc aag gac    816
Tyr Arg Ala Glu Arg Ser Lys Thr Phe Thr Thr Trp Met Val Lys Asp
            260                 265                 270 ctc cag cat cac tgt gtc atc cac gac gcc tgg agc ggc ctg agg cac    864
Leu Gln His His Cys Val Ile His Asp Ala Trp Ser Gly Leu Arg His
        275                 280                 285 gtg gtg cag ctt cgt gcc cag gag gag ttc ggg caa ggc gag tgg agc    912
Val Val Gln Leu Arg Ala Gln Glu Glu Phe Gly Gln Gly Glu Trp Ser
290                 295                 300 gag tgg agc ccg gag gcc atg ggc acg cct tgg aca gaa tcc agg agt    960
Glu Trp Ser Pro Glu Ala Met Gly Thr Pro Trp Thr Glu Ser Arg Ser
305                 310                 315                 320 cct cca gct gag aac gag gtg tcc acc ccc atg cag gca ctt act act   1008
Pro Pro Ala Glu Asn Glu Val Ser Thr Pro Met Gln Ala Leu Thr Thr
                325                 330                 335 aat aaa gac gat gat aat att ctc ttc                               1035
Asn Lys Asp Asp Asp Asn Ile Leu Phe
            340                 345

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: "IL6R1",
      an artificially synthesized primer sequence
<400> SEQUENCE: 3
ttcgaattcc caccatgctg gccgtcggct gcgcgctgct                         40

<210> SEQ ID NO 4
<211> LENGTH: 36
```

```
<212> TYPE: DNA
<213> ORGANISM: Artificial Sequence
<220> FEATURE:
<223> OTHER INFORMATION: Description of Artificial Sequence: "IL6R2",
      an artificially synthesized primer sequence
<400> SEQUENCE: 4
ttcgaattcg aagagaatat tatcatcgtc tttatt                              36

<210> SEQ ID NO 5
<211> LENGTH: 768
<212> TYPE: DNA
<213> ORGANISM: Artificial Sequence
<220> FEATURE:
<221> NAME/KEY: CDS
<222> LOCATION: (1)..(768)
<220> FEATURE:
<223> OTHER INFORMATION: Description of Artificial Sequence: a designed
      single chain Fv gene sequence
<400> SEQUENCE: 5 cag gtc caa ctg cag gag agc ggt cca ggt ctt gtg aga cct agc cag       48
Gln Val Gln Leu Gln Glu Ser Gly Pro Gly Leu Val Arg Pro Ser Gln
 1               5                  10                  15 acc ctg agc ctg acc tgc acc gtg tct ggc tac tca att acc agc gat       96
Thr Leu Ser Leu Thr Cys Thr Val Ser Gly Tyr Ser Ile Thr Ser Asp
                 20                  25                  30 cat gcc tgg agc tgg gtt cgc cag cca cct gga cga ggt ctt gag tgg      144
His Ala Trp Ser Trp Val Arg Gln Pro Pro Gly Arg Gly Leu Glu Trp
             35                  40                  45 att gga tac att agt tat agt gga atc aca acc tat aat cca tct ctc      192
Ile Gly Tyr Ile Ser Tyr Ser Gly Ile Thr Thr Tyr Asn Pro Ser Leu
         50                  55                  60 aaa tcc aga gtg aca atg ctg aga gac acc agc aag aac cag ttc agc      240
Lys Ser Arg Val Thr Met Leu Arg Asp Thr Ser Lys Asn Gln Phe Ser
 65                  70                  75                  80 ctg aga ctc agc agc gtg aca gcc gcc gac acc gcg gtt tat tat tgt      288
Leu Arg Leu Ser Ser Val Thr Ala Ala Asp Thr Ala Val Tyr Tyr Cys
                 85                  90                  95 gca aga tcc cta gct cgg act acg gct atg gac tac tgg ggt caa ggc      336
Ala Arg Ser Leu Ala Arg Thr Thr Ala Met Asp Tyr Trp Gly Gln Gly
                100                 105                 110 agc ctc gtc aca gtc tcc tca ggt ggt ggt ggt tcg ggt ggt ggt ggt      384
Ser Leu Val Thr Val Ser Ser Gly Gly Gly Gly Ser Gly Gly Gly Gly
            115                 120                 125 tcg ggt ggt ggc gga tcg gac atc cag atg acc cag agc cca agc agc      432
Ser Gly Gly Gly Gly Ser Asp Ile Gln Met Thr Gln Ser Pro Ser Ser
        130                 135                 140 ctg agc gcc agc gtg ggt gac aga gtg acc atc acc tgt aga gcc agc      480
Leu Ser Ala Ser Val Gly Asp Arg Val Thr Ile Thr Cys Arg Ala Ser
145                 150                 155                 160 cag gac atc agc agt tac ctg aat tgg tac cag cag aag cca gga aag      528
Gln Asp Ile Ser Ser Tyr Leu Asn Trp Tyr Gln Gln Lys Pro Gly Lys
                165                 170                 175 gct cca aag ctg ctg atc tac tac acc tcc aga ctg cac tct ggt gtg      576
Ala Pro Lys Leu Leu Ile Tyr Tyr Thr Ser Arg Leu His Ser Gly Val
            180                 185                 190 cca agc aga ttc agc ggt agc ggt agc ggt acc gac ttc acc ttc acc      624
Pro Ser Arg Phe Ser Gly Ser Gly Ser Gly Thr Asp Phe Thr Phe Thr
        195                 200                 205 atc agc agc ctc cag cca gag gac atc gct acc tac tac tgc caa cag      672
Ile Ser Ser Leu Gln Pro Glu Asp Ile Ala Thr Tyr Tyr Cys Gln Gln
    210                 215                 220 ggt aac acg ctt cca tac acg ttc ggc caa ggg acc aag gtg gaa atc      720
```

```
Gly Asn Thr Leu Pro Tyr Thr Phe Gly Gln Gly Thr Lys Val Glu Ile
225                 230                 235                 240 aaa cga act gtg gct gca cca tct gtc ttc atc ttc ccg cca tct gat    768
Lys Arg Thr Val Ala Ala Pro Ser Val Phe Ile Phe Pro Pro Ser Asp
                245                 250                 255
```

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: "TMT1",
      an artificially synthesized primer sequence
<400> SEQUENCE: 6
ggtgtcgact cccaggtcca actgcaggag ag                                 32

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: "LINK1",
      an artificially synthesized primer sequence
<400> SEQUENCE: 7
ctcgtcacag tctcctcagg tggtggtggt tc                                 32

<210> SEQ ID NO 8
<211> LENGTH: 38
<212> TYPE: DNA
<213> ORGANISM: Artificial Sequence
<220> FEATURE:
<223> OTHER INFORMATION: Description of Artificial Sequence: "LINK3",
      an artificially synthesized primer sequence
<400> SEQUENCE: 8
gacatccaga tgacccagag cccaagcagc ctgagcgc                           38

<210> SEQ ID NO 9
<211> LENGTH: 63
<212> TYPE: DNA
<213> ORGANISM: Artificial Sequence
<220> FEATURE:
<223> OTHER INFORMATION: Description of Artificial Sequence: "SCP-C",
      an artificially synthesized primer sequence
<400> SEQUENCE: 9
gctgaattct tattatttat cgtcatcgtc tttgtagtca agcttatcag atggcgggaa   60
gat                                                                 63

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: FLAG
      peptide
<400> SEQUENCE: 10

```
Met Asp Tyr Lys Asp Asp Asp Asp Lys
 1               5
```

<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence: "LINK2",
      an artificially synthesized primer sequence
<400> SEQUENCE: 11

```
aaccaccacc acctgaggag actgtgacga ggct                          34
```

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: "LINK4",
     an artificially synthesized primer sequence
<400> SEQUENCE: 12

```
aggctgcttg ggctctgggt catctggatg tccga                         35
```

<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence: "TMT2",
     an artificially synthesized primer sequence
<400> SEQUENCE: 13

```
atccgcggcc gcttattatt tatcgtcatc gtcttt                        36
```

<210> SEQ ID NO 14
<211> LENGTH: 19
<212> TYPE: PRT
<213> ORGANISM: Artificial Sequence
<220> FEATURE:
<223> OTHER INFORMATION: Description of Artificial Sequence: leader
     sequence
<400> SEQUENCE: 14

```
Met Gly Trp Ser Cys Ile Ile Leu Phe Leu Val Ala Thr Ala Thr Gly
 1               5                  10                  15

Val Asp Ser
```

<210> SEQ ID NO 15
<211> LENGTH: 106
<212> TYPE: DNA
<213> ORGANISM: Artificial Sequence
<220> FEATURE:
<223> OTHER INFORMATION: Description of Artificial Sequence: "S-FLAG1",
     an artificially synthesized oligonucleotide sequence
<400> SEQUENCE: 15

```
aattcccacc atgggatgga gctgtatcat cctcttcttg gtagcaacag ctacaggtgt    60
cgactccgac tacaaagacg atgacgataa aggtaccgcg gccgcg                 106
```

<210> SEQ ID NO 16
<211> LENGTH: 106
<212> TYPE: DNA
<213> ORGANISM: Artificial Sequence
<220> FEATURE:
<223> OTHER INFORMATION: Description of Artificial Sequence: "S-FLAG2",
     an artificially synthesized oligonucleotide sequence
<400> SEQUENCE: 16

```
gatccgcggc cgcggtacct ttatcgtcat cgtctttgta gtcggagtcg acacctgtag    60
ctgttgctac caagaagagg atgatacagc tccatcccat ggtggg                 106
```

<210> SEQ ID NO 17
<211> LENGTH: 2995
<212> TYPE: DNA
<213> ORGANISM: Mus musculus
<220> FEATURE:
<221> NAME/KEY: CDS
<222> LOCATION: (29)..(2839)

-continued

<400> SEQUENCE: 17

```
gaattccgga catctagagg cagcgaactt gtttccgatt catgctttat catttcttaa      60
tttcgtatgt tgggaacatc cctgcaag atg tca gca cca agg att tgg cta        112
                              Met Ser Ala Pro Arg Ile Trp Leu
                                1               5 gcg caa gct ttg ctt ttt ttc ctc acc act gaa tct ata ggt caa ctt       160
Ala Gln Ala Leu Leu Phe Phe Leu Thr Thr Glu Ser Ile Gly Gln Leu
     10                  15                  20 ttg gaa ccg tgt ggt tac atc tac cct gaa ttt cca gtt gtc cag cgc       208
Leu Glu Pro Cys Gly Tyr Ile Tyr Pro Glu Phe Pro Val Val Gln Arg
 25                  30                  35                  40 ggc tcg aac ttc act gcc att tgt gtg ctg aag gag gcg tgt ctg cag       256
Gly Ser Asn Phe Thr Ala Ile Cys Val Leu Lys Glu Ala Cys Leu Gln
                 45                  50                  55 cat tac tac gtg aat gcc agc tac atc gtg tgg aag acc aac cat gct       304
His Tyr Tyr Val Asn Ala Ser Tyr Ile Val Trp Lys Thr Asn His Ala
             60                  65                  70 gct gtt ccc agg gag cag gtc act gtc atc aac aga acc acg tcc agt       352
Ala Val Pro Arg Glu Gln Val Thr Val Ile Asn Arg Thr Thr Ser Ser
         75                  80                  85 gtc acg ttc aca gac gtg gtc ctc ccg agc gtg cag ctc acc tgc aac       400
Val Thr Phe Thr Asp Val Val Leu Pro Ser Val Gln Leu Thr Cys Asn
     90                  95                 100 atc ctg tcc ttt ggg cag atc gag cag aat gtg tat gga gtc acc atg       448
Ile Leu Ser Phe Gly Gln Ile Glu Gln Asn Val Tyr Gly Val Thr Met
105                 110                 115                 120 ctt tca ggc ttt cct cca gat aaa cct aca aat ttg act tgc att gtg       496
Leu Ser Gly Phe Pro Pro Asp Lys Pro Thr Asn Leu Thr Cys Ile Val
                125                 130                 135 aat gag ggg aag aat atg ctg tgc cag tgg gac ccc gga agg gag act       544
Asn Glu Gly Lys Asn Met Leu Cys Gln Trp Asp Pro Gly Arg Glu Thr
            140                 145                 150 tac ctt gaa aca aac tac act ttg aaa tca gag tgg gca aca gag aag       592
Tyr Leu Glu Thr Asn Tyr Thr Leu Lys Ser Glu Trp Ala Thr Glu Lys
        155                 160                 165 ttt cct gat tgc cag tca aag cat ggc act tca tgt atg gtc agc tac       640
Phe Pro Asp Cys Gln Ser Lys His Gly Thr Ser Cys Met Val Ser Tyr
    170                 175                 180 atg ccc acc tat tat gtc aac att gaa gtc tgg gtg gaa gca gag aat       688
Met Pro Thr Tyr Tyr Val Asn Ile Glu Val Trp Val Glu Ala Glu Asn
185                 190                 195                 200 gcc ctt ggg aag gtc tcc tca gag tct atc aat ttt gac ccc gtg gat       736
Ala Leu Gly Lys Val Ser Ser Glu Ser Ile Asn Phe Asp Pro Val Asp
                205                 210                 215 aaa gtg aaa ccc acc cca cca tat aat tta tca gtg acc aac tca gaa       784
Lys Val Lys Pro Thr Pro Pro Tyr Asn Leu Ser Val Thr Asn Ser Glu
            220                 225                 230 gaa tta tcc agt ata tta aag cta tca tgg gtc agt tca ggg ctg ggc       832
Glu Leu Ser Ser Ile Leu Lys Leu Ser Trp Val Ser Ser Gly Leu Gly
        235                 240                 245 ggt ctt tta gat cta aag tct gac atc caa tat agg acc aaa gat gcc       880
Gly Leu Leu Asp Leu Lys Ser Asp Ile Gln Tyr Arg Thr Lys Asp Ala
    250                 255                 260 tca act tgg atc cag gtc cct ctt gaa gat aca atg tct cct cga act       928
Ser Thr Trp Ile Gln Val Pro Leu Glu Asp Thr Met Ser Pro Arg Thr
265                 270                 275                 280 tcc ttc act gtg cag gac ctc aag cct ttt aca gaa tat gtg ttt agg       976
Ser Phe Thr Val Gln Asp Leu Lys Pro Phe Thr Glu Tyr Val Phe Arg
                285                 290                 295
```

| | |
|---|---|
| atc cgg tcc att aag gac agt ggg aag ggc tac tgg agt gac tgg agt<br>Ile Arg Ser Ile Lys Asp Ser Gly Lys Gly Tyr Trp Ser Asp Trp Ser<br>300 305 310 | 1024 |
| gag gag gct agt ggg acc aca tac gaa gac aga cca tcc aga cca cca<br>Glu Glu Ala Ser Gly Thr Thr Tyr Glu Asp Arg Pro Ser Arg Pro Pro<br>315 320 325 | 1072 |
| agt ttc tgg tat aag aca aat cca tcc cat ggg cag gaa tat aga tct<br>Ser Phe Trp Tyr Lys Thr Asn Pro Ser His Gly Gln Glu Tyr Arg Ser<br>330 335 340 | 1120 |
| gta cgg ctc ata tgg aag gca ctg cct ctt tct gaa gcc aat ggg aaa<br>Val Arg Leu Ile Trp Lys Ala Leu Pro Leu Ser Glu Ala Asn Gly Lys<br>345 350 355 360 | 1168 |
| atc ttg gat tat gaa gtg att ctt acg cag tca aag tcc gtc tca caa<br>Ile Leu Asp Tyr Glu Val Ile Leu Thr Gln Ser Lys Ser Val Ser Gln<br>365 370 375 | 1216 |
| acg tac aca gtc act ggc aca gag ctg acc gtg aat ctc acc aat gac<br>Thr Tyr Thr Val Thr Gly Thr Glu Leu Thr Val Asn Leu Thr Asn Asp<br>380 385 390 | 1264 |
| cgc tat gtc gcg tct cta gca gca aga aac aag gtg ggc aaa tca gct<br>Arg Tyr Val Ala Ser Leu Ala Ala Arg Asn Lys Val Gly Lys Ser Ala<br>395 400 405 | 1312 |
| gca gct gtc ctc acc atc ccc agc ccc cac gtc aca gct gct tat tct<br>Ala Ala Val Leu Thr Ile Pro Ser Pro His Val Thr Ala Ala Tyr Ser<br>410 415 420 | 1360 |
| gta gtg aat ctt aaa gca ttt cca aaa gat aac ctg ctc tgg gtg gaa<br>Val Val Asn Leu Lys Ala Phe Pro Lys Asp Asn Leu Leu Trp Val Glu<br>425 430 435 440 | 1408 |
| tgg aca cct cca cct aaa ccc gtg agc aag tac atc tta gag tgg tgt<br>Trp Thr Pro Pro Pro Lys Pro Val Ser Lys Tyr Ile Leu Glu Trp Cys<br>445 450 455 | 1456 |
| gtg ttg tca gag aac gca ccc tgt gtt gaa gac tgg cag cag gaa gac<br>Val Leu Ser Glu Asn Ala Pro Cys Val Glu Asp Trp Gln Gln Glu Asp<br>460 465 470 | 1504 |
| gct acc gtg aat cgg acc cac ttg aga gga cgc ctc ctg gag agc aag<br>Ala Thr Val Asn Arg Thr His Leu Arg Gly Arg Leu Leu Glu Ser Lys<br>475 480 485 | 1552 |
| tgc tat caa atc aca gta act ccc gta ttc gcc acg ggg ccc gga ggc<br>Cys Tyr Gln Ile Thr Val Thr Pro Val Phe Ala Thr Gly Pro Gly Gly<br>490 495 500 | 1600 |
| tct gag tcc ttg aag gcg tac ctc aaa caa gcc gct cct gcc aga gga<br>Ser Glu Ser Leu Lys Ala Tyr Leu Lys Gln Ala Ala Pro Ala Arg Gly<br>505 510 515 520 | 1648 |
| ccg act gtt cgg aca aag aaa gtg ggg aaa aat gaa gct gtc tta gcg<br>Pro Thr Val Arg Thr Lys Lys Val Gly Lys Asn Glu Ala Val Leu Ala<br>525 530 535 | 1696 |
| tgg gac cag att cct gtg gac gac cag aat ggc ttc att aga aac tac<br>Trp Asp Gln Ile Pro Val Asp Asp Gln Asn Gly Phe Ile Arg Asn Tyr<br>540 545 550 | 1744 |
| tcc ata tct tac aga acc agc gtg gga aag gag atg gtt gtg cat gtg<br>Ser Ile Ser Tyr Arg Thr Ser Val Gly Lys Glu Met Val Val His Val<br>555 560 565 | 1792 |
| gat tct tct cac acg gag tac acg ctg tcc tct ctg agt agt gat acg<br>Asp Ser Ser His Thr Glu Tyr Thr Leu Ser Ser Leu Ser Ser Asp Thr<br>570 575 580 | 1840 |
| ttg tac atg gtc cga atg gcc gcg tac aca gat gaa ggt ggg aaa gat<br>Leu Tyr Met Val Arg Met Ala Ala Tyr Thr Asp Glu Gly Gly Lys Asp<br>585 590 595 600 | 1888 |
| ggg ccg gaa ttc act ttt aca aca cca aag ttc gct caa gga gaa ata<br>Gly Pro Glu Phe Thr Phe Thr Thr Pro Lys Phe Ala Gln Gly Glu Ile<br> | 1936 |

-continued

```
              605                 610                 615
gaa gcc ata gtc gtg cct gtg tgc tta gcc ttc ctc ctg aca acc ctg      1984
Glu Ala Ile Val Val Pro Val Cys Leu Ala Phe Leu Leu Thr Thr Leu
            620                 625                 630 ctg ggc gtc ttg ttc tgc ttt aac aaa cga gac cta att aaa aaa cac      2032
Leu Gly Val Leu Phe Cys Phe Asn Lys Arg Asp Leu Ile Lys Lys His
            635                 640                 645 atc tgg cct aat gtt cct gat cct tcc aag agt cat att gcc cag tgg      2080
Ile Trp Pro Asn Val Pro Asp Pro Ser Lys Ser His Ile Ala Gln Trp
650                 655                 660 tca cct cac acc ccc cca agg cac aat ttt aac tcc aaa gat caa atg      2128
Ser Pro His Thr Pro Pro Arg His Asn Phe Asn Ser Lys Asp Gln Met
665                 670                 675                 680 tac tcg gac ggc aat ttc act gat gta agc gtt gtg gaa ata gaa gca      2176
Tyr Ser Asp Gly Asn Phe Thr Asp Val Ser Val Val Glu Ile Glu Ala
                685                 690                 695 aac aac aag aag cct tgt cca gat gac ctg aag tcc gtg gac ctg ttc      2224
Asn Asn Lys Lys Pro Cys Pro Asp Asp Leu Lys Ser Val Asp Leu Phe
            700                 705                 710 aag aag gag aaa gtg agt aca gaa ggg cac agc agt ggc atc ggg ggc      2272
Lys Lys Glu Lys Val Ser Thr Glu Gly His Ser Ser Gly Ile Gly Gly
            715                 720                 725 tct tca tgc atg tcc tcc tcc agg ccc agc atc tcc agc aac gag gag      2320
Ser Ser Cys Met Ser Ser Ser Arg Pro Ser Ile Ser Ser Asn Glu Glu
730                 735                 740 aat gag tct gct cag agc acc gcc agc acg gtc gag tac tcc act gtg      2368
Asn Glu Ser Ala Gln Ser Thr Ala Ser Thr Val Glu Tyr Ser Thr Val
745                 750                 755                 760 gtg cac agc ggc tac agg cac cag gtc ccg tcc gtg caa gtg ttc tca      2416
Val His Ser Gly Tyr Arg His Gln Val Pro Ser Val Gln Val Phe Ser
                765                 770                 775 agg tcc gag tcc acc cag ccc ctg cta gac tcg gag gag cgg cca gaa      2464
Arg Ser Glu Ser Thr Gln Pro Leu Leu Asp Ser Glu Glu Arg Pro Glu
            780                 785                 790 gac ctg cag ctg gtg gat agt gta gac ggt ggg gat gag atc ttg ccc      2512
Asp Leu Gln Leu Val Asp Ser Val Asp Gly Gly Asp Glu Ile Leu Pro
            795                 800                 805 agg caa ccg tat ttc aag cag aac tgc agt cag cct gaa gcc tgt cca      2560
Arg Gln Pro Tyr Phe Lys Gln Asn Cys Ser Gln Pro Glu Ala Cys Pro
            810                 815                 820 gag att tca cat ttt gaa agg tca aac cag gtt ttg tcc ggc aat gag      2608
Glu Ile Ser His Phe Glu Arg Ser Asn Gln Val Leu Ser Gly Asn Glu
825                 830                 835                 840 gag gat ttt gtc aga ctg aag cag cag cag gtt tca gat cac att tct      2656
Glu Asp Phe Val Arg Leu Lys Gln Gln Gln Val Ser Asp His Ile Ser
                845                 850                 855 cag ccc tat gga tcc gag caa cgg agg ctg ttt cag gaa ggc tct aca      2704
Gln Pro Tyr Gly Ser Glu Gln Arg Arg Leu Phe Gln Glu Gly Ser Thr
            860                 865                 870 gcg gat gct ctt ggc acg ggg gct gat gga cag atg gag aga ttt gaa      2752
Ala Asp Ala Leu Gly Thr Gly Ala Asp Gly Gln Met Glu Arg Phe Glu
            875                 880                 885 tct gtt gga atg gag acc aca att gat gaa gaa att ccc aaa agt tac      2800
Ser Val Gly Met Glu Thr Thr Ile Asp Glu Glu Ile Pro Lys Ser Tyr
            890                 895                 900 ttg cca cag act gta aga caa ggt ggc tac atg ccg cag tgaaggactg      2849
Leu Pro Gln Thr Val Arg Gln Gly Gly Tyr Met Pro Gln
905                 910                 915 gctcctgaac ttcagcagga actgcaaaat aaagctaaag acgagtggct tcagatgaga   2909
```

-continued

```
aacagtcctc actccctgaa gataggcatt gcctctaagg acaaagtcac acctgggccg      2969
tctccattcc agagtagctg gaattc                                           2995
```

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: "mgp1",
    an artificially synthesized primer sequence
<400> SEQUENCE: 18

```
cccaagcttg aattcacttt tacaaca                                            27
```

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence: "mgp3",
    an artificially synthesized primer sequence
<400> SEQUENCE: 19

```
tttgcggccg cgaattccag ctactctgg                                          29
```

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: "mgp2",
    an artificially synthesized primer sequence
<400> SEQUENCE: 20

```
cccaagcttg aattcaaaaa acacatctgg ctt                                     33
```

<210> SEQ ID NO 21
<211> LENGTH: 1662
<212> TYPE: DNA
<213> ORGANISM: Artificial Sequence
<220> FEATURE:
<221> NAME/KEY: CDS
<222> LOCATION: (11)..(1648)
<220> FEATURE:
<223> OTHER INFORMATION: Description of Artificial Sequence:
    "hPM1-BvGS3 ", a designed single chain Fv gene sequence
<400> SEQUENCE: 21

```
gaattccacc atg gga tgg agc tgt atc atc ctc ttc ttg gta gca aca            49
        Met Gly Trp Ser Cys Ile Ile Leu Phe Leu Val Ala Thr
         1               5                  10 gct aca ggt gtc gac tcc cag gtc caa ctg cag gag agc ggt cca ggt           97
Ala Thr Gly Val Asp Ser Gln Val Gln Leu Gln Glu Ser Gly Pro Gly
 15                  20                  25 ctt gtg aga cct agc cag acc ctg agc ctg acc tgc acc gtg tct ggc          145
Leu Val Arg Pro Ser Gln Thr Leu Ser Leu Thr Cys Thr Val Ser Gly
 30                  35                  40                  45 tac tca att acc agc gat cat gcc tgg agc tgg gtt cgc cag cca cct          193
Tyr Ser Ile Thr Ser Asp His Ala Trp Ser Trp Val Arg Gln Pro Pro
                 50                  55                  60 gga cga ggt ctt gag tgg att gga tac att agt tat agt gga atc aca          241
Gly Arg Gly Leu Glu Trp Ile Gly Tyr Ile Ser Tyr Ser Gly Ile Thr
             65                  70                  75 acc tat aat cca tct ctc aaa tcc aga gtg aca atg ctg aga gac acc          289
Thr Tyr Asn Pro Ser Leu Lys Ser Arg Val Thr Met Leu Arg Asp Thr
         80                  85                  90 agc aag aac cag ttc agc ctg aga ctc agc agc gtg aca gcc gcc gac          337
```

-continued

```
Ser Lys Asn Gln Phe Ser Leu Arg Leu Ser Ser Val Thr Ala Ala Asp
     95                 100                 105 acc gcg gtt tat tat tgt gca aga tcc cta gct cgg act acg gct atg      385
Thr Ala Val Tyr Tyr Cys Ala Arg Ser Leu Ala Arg Thr Thr Ala Met
110             115                 120                 125 gac tac tgg ggt caa ggc agc ctc gtc aca gtc tcc tca ggt ggt ggt      433
Asp Tyr Trp Gly Gln Gly Ser Leu Val Thr Val Ser Ser Gly Gly Gly
                130                 135                 140 ggt tcg ggt ggt ggt ggt tcg ggt ggt ggc gga tcg gac atc cag atg      481
Gly Ser Gly Gly Gly Gly Ser Gly Gly Gly Gly Ser Asp Ile Gln Met
            145                 150                 155 acc cag agc cca agc agc ctg agc gcc agc gtg ggt gac aga gtg acc      529
Thr Gln Ser Pro Ser Ser Leu Ser Ala Ser Val Gly Asp Arg Val Thr
        160                 165                 170 atc acc tgt aga gcc agc cag gac atc agc agt tac ctg aat tgg tac      577
Ile Thr Cys Arg Ala Ser Gln Asp Ile Ser Ser Tyr Leu Asn Trp Tyr
    175                 180                 185 cag cag aag cca gga aag gct cca aag ctg ctg atc tac tac acc tcc      625
Gln Gln Lys Pro Gly Lys Ala Pro Lys Leu Leu Ile Tyr Tyr Thr Ser
190                 195                 200                 205 aga ctg cac tct ggt gtg cca agc aga ttc agc ggt agc ggt agc ggt      673
Arg Leu His Ser Gly Val Pro Ser Arg Phe Ser Gly Ser Gly Ser Gly
                210                 215                 220 acc gac ttc acc ttc acc atc agc agc ctc cag cca gag gac atc gct      721
Thr Asp Phe Thr Phe Thr Ile Ser Ser Leu Gln Pro Glu Asp Ile Ala
            225                 230                 235 acc tac tac tgc caa cag ggt aac acg ctt cca tac acg ttc ggc caa      769
Thr Tyr Tyr Cys Gln Gln Gly Asn Thr Leu Pro Tyr Thr Phe Gly Gln
        240                 245                 250 ggg acc aag gtg gaa atc aaa tct aga ggt ggt ggt ggt tcg ggt ggt      817
Gly Thr Lys Val Glu Ile Lys Ser Arg Gly Gly Gly Gly Ser Gly Gly
    255                 260                 265 ggt ggt tcg ggt ggt ggc gga tcg gtc gac tcc cag gtc caa ctg cag      865
Gly Gly Ser Gly Gly Gly Gly Ser Val Asp Ser Gln Val Gln Leu Gln
270                 275                 280                 285 gag agc ggt cca ggt ctt gtg aga cct agc cag acc ctg agc ctg acc      913
Glu Ser Gly Pro Gly Leu Val Arg Pro Ser Gln Thr Leu Ser Leu Thr
                290                 295                 300 tgc acc gtg tct ggc tac tca att acc agc gat cat gcc tgg agc tgg      961
Cys Thr Val Ser Gly Tyr Ser Ile Thr Ser Asp His Ala Trp Ser Trp
            305                 310                 315 gtt cgc cag cca cct gga cga ggt ctt gag tgg att gga tac att agt     1009
Val Arg Gln Pro Pro Gly Arg Gly Leu Glu Trp Ile Gly Tyr Ile Ser
        320                 325                 330 tat agt gga atc aca acc tat aat cca tct ctc aaa tcc aga gtg aca     1057
Tyr Ser Gly Ile Thr Thr Tyr Asn Pro Ser Leu Lys Ser Arg Val Thr
    335                 340                 345 atg ctg aga gac acc agc aag aac cag ttc agc ctg aga ctc agc agc     1105
Met Leu Arg Asp Thr Ser Lys Asn Gln Phe Ser Leu Arg Leu Ser Ser
350                 355                 360                 365 gtg aca gcc gcc gac acc gcg gtt tat tat tgt gca aga tcc cta gct     1153
Val Thr Ala Ala Asp Thr Ala Val Tyr Tyr Cys Ala Arg Ser Leu Ala
                370                 375                 380 cgg act acg gct atg gac tac tgg ggt caa ggc agc ctc gtc aca gtc     1201
Arg Thr Thr Ala Met Asp Tyr Trp Gly Gln Gly Ser Leu Val Thr Val
            385                 390                 395 tcc tca ggt ggt ggt ggt tcg ggt ggt ggt ggt tcg ggt ggt ggc gga     1249
Ser Ser Gly Gly Gly Gly Ser Gly Gly Gly Gly Ser Gly Gly Gly Gly
        400                 405                 410 tcg gac atc cag atg acc cag agc cca agc agc ctg agc gcc agc gtg     1297
```

```
                                                                          -continued Ser Asp Ile Gln Met Thr Gln Ser Pro Ser Ser Leu Ser Ala Ser Val
    415                 420                 425 ggt gac aga gtg acc atc acc tgt aga gcc agc cag gac atc agc agt        1345
Gly Asp Arg Val Thr Ile Thr Cys Arg Ala Ser Gln Asp Ile Ser Ser
430                 435                 440                 445 tac ctg aat tgg tac cag cag aag cca gga aag gct cca aag ctg ctg        1393
Tyr Leu Asn Trp Tyr Gln Gln Lys Pro Gly Lys Ala Pro Lys Leu Leu
                450                 455                 460 atc tac tac acc tcc aga ctg cac tct ggt gtg cca agc aga ttc agc        1441
Ile Tyr Tyr Thr Ser Arg Leu His Ser Gly Val Pro Ser Arg Phe Ser
            465                 470                 475 ggt agc ggt agc ggt acc gac ttc acc ttc acc atc agc agc ctc cag        1489
Gly Ser Gly Ser Gly Thr Asp Phe Thr Phe Thr Ile Ser Ser Leu Gln
        480                 485                 490 cca gag gac atc gct acc tac tac tgc caa cag ggt aac acg ctt cca        1537
Pro Glu Asp Ile Ala Thr Tyr Tyr Cys Gln Gln Gly Asn Thr Leu Pro
    495                 500                 505 tac acg ttc ggc caa ggg acc aag gtg gaa atc aaa cga act gtg gct        1585
Tyr Thr Phe Gly Gln Gly Thr Lys Val Glu Ile Lys Arg Thr Val Ala
510                 515                 520                 525 gca cca tct gtc ttc atc ttc ccg cca tct gat aag ctt gac tac aaa        1633
Ala Pro Ser Val Phe Ile Phe Pro Pro Ser Asp Lys Leu Asp Tyr Lys
                530                 535                 540 gac gat gac gat aaa taataagcgg ccgc                                    1662
Asp Asp Asp Asp Lys
            545

<210> SEQ ID NO 22
<211> LENGTH: 72
<212> TYPE: DNA
<213> ORGANISM: Artificial Sequence
<220> FEATURE:
<223> OTHER INFORMATION: Description of Artificial Sequence: "BvGS3",
      an artificially synthesized primer sequence
<400> SEQUENCE: 22
ggagtcgacc gatccgccac cacccgaacc accaccaccc gaaccaccac cacctttgat       60
ttccaccttg gt                                                          72

<210> SEQ ID NO 23
<211> LENGTH: 780
<212> TYPE: DNA
<213> ORGANISM: Artificial Sequence
<220> FEATURE:
<221> NAME/KEY: CDS
<222> LOCATION: (1)..(780)
<220> FEATURE:
<223> OTHER INFORMATION: Description of Artificial Sequence:
      "shPM1((EL)", a designed single chain Fv gene sequence
<400> SEQUENCE: 23 atg gga tgg agc tgt atc atc ctc ttc ttg gta gca aca gct aca ggt         48
Met Gly Trp Ser Cys Ile Ile Leu Phe Leu Val Ala Thr Ala Thr Gly
1               5                   10                  15 gtc gac tcc cag gtc caa ctg cag gag agc ggt cca ggt ctt gtg aga         96
Val Asp Ser Gln Val Gln Leu Gln Glu Ser Gly Pro Gly Leu Val Arg
            20                  25                  30 cct agc cag acc ctg agc ctg acc tgc acc gtg tct ggc tac tca att        144
Pro Ser Gln Thr Leu Ser Leu Thr Cys Thr Val Ser Gly Tyr Ser Ile
        35                  40                  45 acc agc gat cat gcc tgg agc tgg gtt cgc cag cca cct gga cga ggt        192
Thr Ser Asp His Ala Trp Ser Trp Val Arg Gln Pro Pro Gly Arg Gly
    50                  55                  60 ctt gag tgg att gga tac att agt tat agt gga atc aca acc tat aat        240
```

-continued

```
Leu Glu Trp Ile Gly Tyr Ile Ser Tyr Ser Gly Ile Thr Thr Tyr Asn
 65                  70                  75                  80 cca tct ctc aaa tcc aga gtg aca atg ctg aga gac acc agc aag aac    288
Pro Ser Leu Lys Ser Arg Val Thr Met Leu Arg Asp Thr Ser Lys Asn
                 85                  90                  95 cag ttc agc ctg aga ctc agc agc gtg aca gcc gcc gac acc gcg gtt    336
Gln Phe Ser Leu Arg Leu Ser Ser Val Thr Ala Ala Asp Thr Ala Val
            100                 105                 110 tat tat tgt gca aga tcc cta gct cgg act acg gct atg gac tac tgg    384
Tyr Tyr Cys Ala Arg Ser Leu Ala Arg Thr Thr Ala Met Asp Tyr Trp
        115                 120                 125 ggt caa ggc agc ctc gtc aca gtc tcc tca ggt ggt ggt ggt tcg ggt    432
Gly Gln Gly Ser Leu Val Thr Val Ser Ser Gly Gly Gly Gly Ser Gly
    130                 135                 140 ggt ggt ggt tcg ggt ggt ggc gga tcg gac atc cag atg acc cag agc    480
Gly Gly Gly Ser Gly Gly Gly Gly Ser Asp Ile Gln Met Thr Gln Ser
145                 150                 155                 160 cca agc agc ctg agc gcc agc gtg ggt gac aga gtg acc atc acc tgt    528
Pro Ser Ser Leu Ser Ala Ser Val Gly Asp Arg Val Thr Ile Thr Cys
                165                 170                 175 aga gcc agc cag gac atc agc agt tac ctg aat tgg tac cag cag aag    576
Arg Ala Ser Gln Asp Ile Ser Ser Tyr Leu Asn Trp Tyr Gln Gln Lys
            180                 185                 190 cca gga aag gct cca aag ctg ctg atc tac tac acc tcc aga ctg cac    624
Pro Gly Lys Ala Pro Lys Leu Leu Ile Tyr Tyr Thr Ser Arg Leu His
        195                 200                 205 tct ggt gtg cca agc aga ttc agc ggt agc ggt agc ggt acc gac ttc    672
Ser Gly Val Pro Ser Arg Phe Ser Gly Ser Gly Ser Gly Thr Asp Phe
    210                 215                 220 acc ttc acc atc agc agc ctc cag cca gag gac atc gct acc tac tac    720
Thr Phe Thr Ile Ser Ser Leu Gln Pro Glu Asp Ile Ala Thr Tyr Tyr
225                 230                 235                 240 tgc caa cag gga aat act tta cca tac acg ttc ggc caa ggg acc aag    768
Cys Gln Gln Gly Asn Thr Leu Pro Tyr Thr Phe Gly Gln Gly Thr Lys
                245                 250                 255 gtg gaa atc aaa                                                    780
Val Glu Ile Lys
            260

<210> SEQ ID NO 24
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 24 cga act gtg gct gca cca tct gtc ttc atc ttc ccg cca tct gat gag     48
Arg Thr Val Ala Ala Pro Ser Val Phe Ile Phe Pro Pro Ser Asp Glu
  1               5                  10                  15 cag ttg aaa tct gga act gcc tct gtt gtg tgc ctg ctg aat aac ttc     96
Gln Leu Lys Ser Gly Thr Ala Ser Val Val Cys Leu Leu Asn Asn Phe
             20                  25                  30 tat ccc aga gag gcc aaa gta cag tgg aag gtg gat aac gcc ctc caa    144
Tyr Pro Arg Glu Ala Lys Val Gln Trp Lys Val Asp Asn Ala Leu Gln
         35                  40                  45 tcg ggt aac tcc cag gag agt gtc aca gag cag gac agc aag gac agc    192
Ser Gly Asn Ser Gln Glu Ser Val Thr Glu Gln Asp Ser Lys Asp Ser
     50                  55                  60 acc tac agc ctc agc agc acc ctg acg ctg agc aaa gca gac tac gag    240
```

```
Thr Tyr Ser Leu Ser Ser Thr Leu Thr Leu Ser Lys Ala Asp Tyr Glu
 65                  70                  75                  80 aaa cac aaa gtc tac gcc tgc gaa gtc acc cat cag ggc ctg agc tcg          288
Lys His Lys Val Tyr Ala Cys Glu Val Thr His Gln Gly Leu Ser Ser
                 85                  90                  95 ccc gtc aca aag agc ttc aac agg gga gag tct                              321
Pro Val Thr Lys Ser Phe Asn Arg Gly Glu Ser
            100                 105

<210> SEQ ID NO 25
<211> LENGTH: 363
<212> TYPE: DNA
<213> ORGANISM: Homo sapiens
<220> FEATURE:
<221> NAME/KEY: CDS
<222> LOCATION: (1)..(363)

<400> SEQUENCE: 25 gtg gcc ctg cac agg ccc gat gtc tac ttg cta cca gcc cgg gag              48
Val Ala Leu His Arg Pro Asp Val Tyr Leu Leu Pro Pro Ala Arg Glu
  1               5                  10                  15 cag ctg aac ctg cgg gag tcg gcc acc atc acg tgc ctg gtg acg ggc          96
Gln Leu Asn Leu Arg Glu Ser Ala Thr Ile Thr Cys Leu Val Thr Gly
                 20                  25                  30 ttc tct ccc gcg gac gtc ttc gtg cag tgg atg cag agg ggg cag ccc          144
Phe Ser Pro Ala Asp Val Phe Val Gln Trp Met Gln Arg Gly Gln Pro
             35                  40                  45 ttg tcc ccg gag aag tat gtg acc agc gcc cca atg cct gag ccc cag          192
Leu Ser Pro Glu Lys Tyr Val Thr Ser Ala Pro Met Pro Glu Pro Gln
         50                  55                  60 gcc cca ggc cgg tac ttc gcc cac agc atc ctg acc gtg tcc gaa gag          240
Ala Pro Gly Arg Tyr Phe Ala His Ser Ile Leu Thr Val Ser Glu Glu
 65                  70                  75                  80 gaa tgg aac acg ggg gag acc tac acc tgc gtg gcc cat gag gcc ctg          288
Glu Trp Asn Thr Gly Glu Thr Tyr Thr Cys Val Ala His Glu Ala Leu
                 85                  90                  95 ccc aac agg gtc acc gag agg acc gtg gac aag tcc acc gag ggg gag          336
Pro Asn Arg Val Thr Glu Arg Thr Val Asp Lys Ser Thr Glu Gly Glu
            100                 105                 110 gtg agc gcc gac gag gag ggc ttt gag                                       363
Val Ser Ala Asp Glu Glu Gly Phe Glu
        115                 120

<210> SEQ ID NO 26
<211> LENGTH: 1101
<212> TYPE: DNA
<213> ORGANISM: Artificial Sequence
<220> FEATURE:
<221> NAME/KEY: CDS
<222> LOCATION: (1)..(1101)
<220> FEATURE:
<223> OTHER INFORMATION: Description of Artificial Sequence:
      "shPM1-Kappa", a designed single chain Fv gene sequence

<400> SEQUENCE: 26 atg gga tgg agc tgt atc atc ctc ttc ttg gta gca aca gct aca ggt          48
Met Gly Trp Ser Cys Ile Ile Leu Phe Leu Val Ala Thr Ala Thr Gly
  1               5                  10                  15 gtc gac tcc cag gtc caa ctg cag gag agc ggt cca ggt ctt gtg aga          96
Val Asp Ser Gln Val Gln Leu Gln Glu Ser Gly Pro Gly Leu Val Arg
                 20                  25                  30 cct agc cag acc ctg agc ctg acc tgc acc gtg tct ggc tac tca att          144
Pro Ser Gln Thr Leu Ser Leu Thr Cys Thr Val Ser Gly Tyr Ser Ile
             35                  40                  45
```

-continued

| | | |
|---|---|---|
| acc agc gat cat gcc tgg agc tgg gtt cgc cag cca cct gga cga ggt<br>Thr Ser Asp His Ala Trp Ser Trp Val Arg Gln Pro Pro Gly Arg Gly<br>    50                            55                        60 | 192 |
| ctt gag tgg att gga tac att agt tat agt gga atc aca acc tat aat<br>Leu Glu Trp Ile Gly Tyr Ile Ser Tyr Ser Gly Ile Thr Thr Tyr Asn<br>65                            70                        75                        80 | 240 |
| cca tct ctc aaa tcc aga gtg aca atg ctg aga gac acc agc aag aac<br>Pro Ser Leu Lys Ser Arg Val Thr Met Leu Arg Asp Thr Ser Lys Asn<br>                        85                        90                        95 | 288 |
| cag ttc agc ctg aga ctc agc agc gtg aca gcc gcc gac acc gcg gtt<br>Gln Phe Ser Leu Arg Leu Ser Ser Val Thr Ala Ala Asp Thr Ala Val<br>                   100                   105                   110 | 336 |
| tat tat tgt gca aga tcc cta gct cgg act acg gct atg gac tac tgg<br>Tyr Tyr Cys Ala Arg Ser Leu Ala Arg Thr Thr Ala Met Asp Tyr Trp<br>        115                    120                   125 | 384 |
| ggt caa ggc agc ctc gtc aca gtc tcc tca ggt ggt ggt ggt tcg ggt<br>Gly Gln Gly Ser Leu Val Thr Val Ser Ser Gly Gly Gly Gly Ser Gly<br>130                          135                        140 | 432 |
| ggt ggt ggt tcg ggt ggt ggc gga tcg gac atc cag atg acc cag agc<br>Gly Gly Gly Ser Gly Gly Gly Gly Ser Asp Ile Gln Met Thr Gln Ser<br>145                          150                        155                   160 | 480 |
| cca agc agc ctg agc gcc agc gtg ggt gac aga gtg acc atc acc tgt<br>Pro Ser Ser Leu Ser Ala Ser Val Gly Asp Arg Val Thr Ile Thr Cys<br>                   165                    170                   175 | 528 |
| aga gcc agc cag gac atc agc agt tac ctg aat tgg tac cag cag aag<br>Arg Ala Ser Gln Asp Ile Ser Ser Tyr Leu Asn Trp Tyr Gln Gln Lys<br>        180                    185                   190 | 576 |
| cca gga aag gct cca aag ctg ctg atc tac tac acc tcc aga ctg cac<br>Pro Gly Lys Ala Pro Lys Leu Leu Ile Tyr Tyr Thr Ser Arg Leu His<br>             195                    200                   205 | 624 |
| tct ggt gtg cca agc aga ttc agc ggt agc ggt agc ggt acc gac ttc<br>Ser Gly Val Pro Ser Arg Phe Ser Gly Ser Gly Ser Gly Thr Asp Phe<br>210                          215                        220 | 672 |
| acc ttc acc atc agc agc ctc cag cca gag gac atc gct acc tac tac<br>Thr Phe Thr Ile Ser Ser Leu Gln Pro Glu Asp Ile Ala Thr Tyr Tyr<br>225                          230                        235                   240 | 720 |
| tgc caa cag gga aat act tta cca tac acg ttc ggc caa ggg acc aag<br>Cys Gln Gln Gly Asn Thr Leu Pro Tyr Thr Phe Gly Gln Gly Thr Lys<br>                   245                    250                   255 | 768 |
| gtg gaa atc aaa cga act gtg gct gca cca tct gtc ttc atc ttc ccg<br>Val Glu Ile Lys Arg Thr Val Ala Ala Pro Ser Val Phe Ile Phe Pro<br>        260                    265                   270 | 816 |
| cca tct gat gag cag ttg aaa tct gga act gcc tct gtt gtg tgc ctg<br>Pro Ser Asp Glu Gln Leu Lys Ser Gly Thr Ala Ser Val Val Cys Leu<br>275                          280                        285 | 864 |
| ctg aat aac ttc tat ccc aga gag gcc aaa gta cag tgg aag gtg gat<br>Leu Asn Asn Phe Tyr Pro Arg Glu Ala Lys Val Gln Trp Lys Val Asp<br>        290                    295                   300 | 912 |
| aac gcc ctc caa tcg ggt aac tcc cag gag agt gtc aca gag cag gac<br>Asn Ala Leu Gln Ser Gly Asn Ser Gln Glu Ser Val Thr Glu Gln Asp<br>305                          310                        315                   320 | 960 |
| agc aag gac agc acc tac agc ctc agc agc acc ctg acg ctg agc aaa<br>Ser Lys Asp Ser Thr Tyr Ser Leu Ser Ser Thr Leu Thr Leu Ser Lys<br>                   325                    330                   335 | 1008 |
| gca gac tac gag aaa cac aaa gtc tac gcc tgc gaa gtc acc cat cag<br>Ala Asp Tyr Glu Lys His Lys Val Tyr Ala Cys Glu Val Thr His Gln<br>        340                    345                   350 | 1056 |
| ggc ctg agc tcg ccc gtc aca aag agc ttc aac agg gga gag tct<br>Gly Leu Ser Ser Pro Val Thr Lys Ser Phe Asn Arg Gly Glu Ser<br>         355                   360                  365 | 1101 |

<210> SEQ ID NO 27
<211> LENGTH: 1143
<212> TYPE: DNA
<213> ORGANISM: Artificial Sequence
<220> FEATURE:
<221> NAME/KEY: CDS
<222> LOCATION: (1)..(1143)
<220> FEATURE:
<223> OTHER INFORMATION: Description of Artificial Sequence: "shPM1-MCH4", a designed single chain Fv gene sequence

<400> SEQUENCE: 27

| | | | | | | | | | | | | | | | | |
|---|---|---|---|---|---|---|---|---|---|---|---|---|---|---|---|---|
| atg | gga | tgg | agc | tgt | atc | atc | ctc | ttc | ttg | gta | gca | aca | gct | aca | ggt | 48 |
| Met | Gly | Trp | Ser | Cys | Ile | Ile | Leu | Phe | Leu | Val | Ala | Thr | Ala | Thr | Gly | |
| 1 | | | | 5 | | | | | 10 | | | | | 15 | | |
| gtc | gac | tcc | cag | gtc | caa | ctg | cag | gag | agc | ggt | cca | ggt | ctt | gtg | aga | 96 |
| Val | Asp | Ser | Gln | Val | Gln | Leu | Gln | Glu | Ser | Gly | Pro | Gly | Leu | Val | Arg | |
| | | | 20 | | | | | 25 | | | | | 30 | | | |
| cct | agc | cag | acc | ctg | agc | ctg | acc | tgc | acc | gtg | tct | ggc | tac | tca | att | 144 |
| Pro | Ser | Gln | Thr | Leu | Ser | Leu | Thr | Cys | Thr | Val | Ser | Gly | Tyr | Ser | Ile | |
| | | 35 | | | | | 40 | | | | | 45 | | | | |
| acc | agc | gat | cat | gcc | tgg | agc | tgg | gtt | cgc | cag | cca | cct | gga | cga | ggt | 192 |
| Thr | Ser | Asp | His | Ala | Trp | Ser | Trp | Val | Arg | Gln | Pro | Pro | Gly | Arg | Gly | |
| | 50 | | | | | 55 | | | | | 60 | | | | | |
| ctt | gag | tgg | att | gga | tac | att | agt | tat | agt | gga | atc | aca | acc | tat | aat | 240 |
| Leu | Glu | Trp | Ile | Gly | Tyr | Ile | Ser | Tyr | Ser | Gly | Ile | Thr | Thr | Tyr | Asn | |
| 65 | | | | | 70 | | | | | 75 | | | | | 80 | |
| cca | tct | ctc | aaa | tcc | aga | gtg | aca | atg | ctg | aga | gac | acc | agc | aag | aac | 288 |
| Pro | Ser | Leu | Lys | Ser | Arg | Val | Thr | Met | Leu | Arg | Asp | Thr | Ser | Lys | Asn | |
| | | | | 85 | | | | | 90 | | | | | 95 | | |
| cag | ttc | agc | ctg | aga | ctc | agc | agc | gtg | aca | gcc | gcc | gac | acc | gcg | gtt | 336 |
| Gln | Phe | Ser | Leu | Arg | Leu | Ser | Ser | Val | Thr | Ala | Ala | Asp | Thr | Ala | Val | |
| | | | 100 | | | | | 105 | | | | | 110 | | | |
| tat | tat | tgt | gca | aga | tcc | cta | gct | cgg | act | acg | gct | atg | gac | tac | tgg | 384 |
| Tyr | Tyr | Cys | Ala | Arg | Ser | Leu | Ala | Arg | Thr | Thr | Ala | Met | Asp | Tyr | Trp | |
| | | 115 | | | | | 120 | | | | | 125 | | | | |
| ggt | caa | ggc | agc | ctc | gtc | aca | gtc | tcc | tca | ggt | ggt | ggt | ggt | tcg | ggt | 432 |
| Gly | Gln | Gly | Ser | Leu | Val | Thr | Val | Ser | Ser | Gly | Gly | Gly | Gly | Ser | Gly | |
| | 130 | | | | | 135 | | | | | 140 | | | | | |
| ggt | ggt | ggt | tcg | ggt | ggt | ggc | gga | tcg | gac | atc | cag | atg | acc | cag | agc | 480 |
| Gly | Gly | Gly | Ser | Gly | Gly | Gly | Gly | Ser | Asp | Ile | Gln | Met | Thr | Gln | Ser | |
| 145 | | | | | 150 | | | | | 155 | | | | | 160 | |
| cca | agc | agc | ctg | agc | gcc | agc | gtg | ggt | gac | aga | gtg | acc | atc | acc | tgt | 528 |
| Pro | Ser | Ser | Leu | Ser | Ala | Ser | Val | Gly | Asp | Arg | Val | Thr | Ile | Thr | Cys | |
| | | | | 165 | | | | | 170 | | | | | 175 | | |
| aga | gcc | agc | cag | gac | atc | agc | agt | tac | ctg | aat | tgg | tac | cag | cag | aag | 576 |
| Arg | Ala | Ser | Gln | Asp | Ile | Ser | Ser | Tyr | Leu | Asn | Trp | Tyr | Gln | Gln | Lys | |
| | | | 180 | | | | | 185 | | | | | 190 | | | |
| cca | gga | aag | gct | cca | aag | ctg | ctg | atc | tac | tac | acc | tcc | aga | ctg | cac | 624 |
| Pro | Gly | Lys | Ala | Pro | Lys | Leu | Leu | Ile | Tyr | Tyr | Thr | Ser | Arg | Leu | His | |
| | | 195 | | | | | 200 | | | | | 205 | | | | |
| tct | ggt | gtg | cca | agc | aga | ttc | agc | ggt | agc | ggt | agc | ggt | acc | gac | ttc | 672 |
| Ser | Gly | Val | Pro | Ser | Arg | Phe | Ser | Gly | Ser | Gly | Ser | Gly | Thr | Asp | Phe | |
| | 210 | | | | | 215 | | | | | 220 | | | | | |
| acc | ttc | acc | atc | agc | agc | ctc | cag | cca | gag | gac | atc | gct | acc | tac | tac | 720 |
| Thr | Phe | Thr | Ile | Ser | Ser | Leu | Gln | Pro | Glu | Asp | Ile | Ala | Thr | Tyr | Tyr | |
| 225 | | | | | 230 | | | | | 235 | | | | | 240 | |
| tgc | caa | cag | gga | aat | act | tta | cca | tac | acg | ttc | ggc | caa | ggg | acc | aag | 768 |
| Cys | Gln | Gln | Gly | Asn | Thr | Leu | Pro | Tyr | Thr | Phe | Gly | Gln | Gly | Thr | Lys | |
| | | | | 245 | | | | | 250 | | | | | 255 | | |
| gtg | gaa | atc | aaa | gtg | gcc | ctg | cac | agg | ccc | gat | gtc | tac | ttg | ctg | cca | 816 |

```
Val Glu Ile Lys Val Ala Leu His Arg Pro Asp Val Tyr Leu Leu Pro
            260                 265                 270 cca gcc cgg gag cag ctg aac ctg cgg gag tcg gcc acc atc acg tgc    864
Pro Ala Arg Glu Gln Leu Asn Leu Arg Glu Ser Ala Thr Ile Thr Cys
        275                 280                 285 ctg gtg acg ggc ttc tct ccc gcg gac gtc ttc gtg cag tgg atg cag    912
Leu Val Thr Gly Phe Ser Pro Ala Asp Val Phe Val Gln Trp Met Gln
    290                 295                 300 agg ggg cag ccc ttg tcc ccg gag aag tat gtg acc agc gcc cca atg    960
Arg Gly Gln Pro Leu Ser Pro Glu Lys Tyr Val Thr Ser Ala Pro Met
305                 310                 315                 320 cct gag ccc cag gcc cca ggc cgg tac ttc gcc cac agc atc ctg acc   1008
Pro Glu Pro Gln Ala Pro Gly Arg Tyr Phe Ala His Ser Ile Leu Thr
                325                 330                 335 gtg tcc gaa gag gaa tgg aac acg ggg gag acc tac acc tgc gtg gcc   1056
Val Ser Glu Glu Glu Trp Asn Thr Gly Glu Thr Tyr Thr Cys Val Ala
            340                 345                 350 cat gag gcc ctg ccc aac agg gtc acc gag agg acc gtg gac aag tcc   1104
His Glu Ala Leu Pro Asn Arg Val Thr Glu Arg Thr Val Asp Lys Ser
        355                 360                 365 acc gag ggg gag gtg agc gcc gac gag gag ggc ttt gag                1143
Thr Glu Gly Glu Val Ser Ala Asp Glu Glu Gly Phe Glu
    370                 375                 380

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence:
      "EF-1", an artificially synthesized primer sequence
<400> SEQUENCE: 28
cagacagtgg ttcaaagt                                                 18

<210> SEQ ID NO 29
<211> LENGTH: 107
<212> TYPE: DNA
<213> ORGANISM: Artificial Sequence
<220> FEATURE:
<223> OTHER INFORMATION: Description of Artificial Sequence:
      "SCP-C2", an artificially synthesized  primer sequence
<400> SEQUENCE: 29
aaagcggccg cttattattt atcgtcatcg tctttgtagt ctgaagcttt gatttccacc   60
ttggtccctt ggccgaacgt gtatggtaaa gtatttccct gttggca                107

<210> SEQ ID NO 30
<211> LENGTH: 1557
<212> TYPE: DNA
<213> ORGANISM: Artificial Sequence
<220> FEATURE:
<221> NAME/KEY: CDS
<222> LOCATION: (1)..(1557)
<220> FEATURE:
<223> OTHER INFORMATION: Description of Artificial Sequence:
      "shPM1((EL)-BvGS3", a designed single chain Fv gene sequence
<400> SEQUENCE: 30 atg gga tgg agc tgt atc atc ctc ttc ttg gta gca aca gct aca ggt     48
Met Gly Trp Ser Cys Ile Ile Leu Phe Leu Val Ala Thr Ala Thr Gly
 1               5                  10                  15 gtc gac tcc cag gtc caa ctg cag gag agc ggt cca ggt ctt gtg aga     96
Val Asp Ser Gln Val Gln Leu Gln Glu Ser Gly Pro Gly Leu Val Arg
            20                  25                  30 cct agc cag acc ctg agc ctg acc tgc acc gtg tct ggc tac tca att    144
```

```
                                                          -continued

Pro Ser Gln Thr Leu Ser Leu Thr Cys Thr Val Ser Gly Tyr Ser Ile
         35                  40                  45 acc agc gat cat gcc tgg agc tgg gtt cgc cag cca cct gga cga ggt          192
Thr Ser Asp His Ala Trp Ser Trp Val Arg Gln Pro Pro Gly Arg Gly
 50                  55                  60 ctt gag tgg att gga tac att agt tat agt gga atc aca acc tat aat          240
Leu Glu Trp Ile Gly Tyr Ile Ser Tyr Ser Gly Ile Thr Thr Tyr Asn
 65                  70                  75                  80 cca tct ctc aaa tcc aga gtg aca atg ctg aga gac acc agc aag aac          288
Pro Ser Leu Lys Ser Arg Val Thr Met Leu Arg Asp Thr Ser Lys Asn
                 85                  90                  95 cag ttc agc ctg aga ctc agc agc gtg aca gcc gcc gac acc gcg gtt          336
Gln Phe Ser Leu Arg Leu Ser Ser Val Thr Ala Ala Asp Thr Ala Val
            100                 105                 110 tat tat tgt gca aga tcc cta gct cgg act acg gct atg gac tac tgg          384
Tyr Tyr Cys Ala Arg Ser Leu Ala Arg Thr Thr Ala Met Asp Tyr Trp
            115                 120                 125 ggt caa ggc agc ctc gtc aca gtc tcc tca ggt ggt ggt ggt tcg ggt          432
Gly Gln Gly Ser Leu Val Thr Val Ser Ser Gly Gly Gly Gly Ser Gly
130                 135                 140 ggt ggt ggt tcg ggt ggt ggc gga tcg gac atc cag atg acc cag agc          480
Gly Gly Gly Ser Gly Gly Gly Gly Ser Asp Ile Gln Met Thr Gln Ser
145                 150                 155                 160 cca agc agc ctg agc gcc agc gtg ggt gac aga gtg acc atc acc tgt          528
Pro Ser Ser Leu Ser Ala Ser Val Gly Asp Arg Val Thr Ile Thr Cys
                165                 170                 175 aga gcc agc cag gac atc agc agt tac ctg aat tgg tac cag cag aag          576
Arg Ala Ser Gln Asp Ile Ser Ser Tyr Leu Asn Trp Tyr Gln Gln Lys
            180                 185                 190 cca gga aag gct cca aag ctg ctg atc tac tac acc tcc aga ctg cac          624
Pro Gly Lys Ala Pro Lys Leu Leu Ile Tyr Tyr Thr Ser Arg Leu His
            195                 200                 205 tct ggt gtg cca agc aga ttc agc ggt agc ggt agc ggt acc gac ttc          672
Ser Gly Val Pro Ser Arg Phe Ser Gly Ser Gly Ser Gly Thr Asp Phe
210                 215                 220 acc ttc acc atc agc agc ctc cag cca gag gac atc gct acc tac tac          720
Thr Phe Thr Ile Ser Ser Leu Gln Pro Glu Asp Ile Ala Thr Tyr Tyr
225                 230                 235                 240 tgc caa cag ggt aac acg ctt cca tac acg ttc ggc caa ggg acc aag          768
Cys Gln Gln Gly Asn Thr Leu Pro Tyr Thr Phe Gly Gln Gly Thr Lys
                245                 250                 255 gtg gaa atc aaa ggt ggt ggt ggt tcg ggt ggt ggt ggt tcg ggt ggt          816
Val Glu Ile Lys Gly Gly Gly Gly Ser Gly Gly Gly Gly Ser Gly Gly
            260                 265                 270 ggc gga tcg gtc gac tcc cag gtc caa ctg cag gag agc ggt cca ggt          864
Gly Gly Ser Val Asp Ser Gln Val Gln Leu Gln Glu Ser Gly Pro Gly
            275                 280                 285 ctt gtg aga cct agc cag acc ctg agc ctg acc tgc acc gtg tct ggc          912
Leu Val Arg Pro Ser Gln Thr Leu Ser Leu Thr Cys Thr Val Ser Gly
290                 295                 300 tac tca att acc agc gat cat gcc tgg agc tgg gtt cgc cag cca cct          960
Tyr Ser Ile Thr Ser Asp His Ala Trp Ser Trp Val Arg Gln Pro Pro
305                 310                 315                 320 gga cga ggt ctt gag tgg att gga tac att agt tat agt gga atc aca          1008
Gly Arg Gly Leu Glu Trp Ile Gly Tyr Ile Ser Tyr Ser Gly Ile Thr
                325                 330                 335 acc tat aat cca tct ctc aaa tcc aga gtg aca atg ctg aga gac acc          1056
Thr Tyr Asn Pro Ser Leu Lys Ser Arg Val Thr Met Leu Arg Asp Thr
            340                 345                 350
```

-continued

```
agc aag aac cag ttc agc ctg aga ctc agc agc gtg aca gcc gcc gac    1104
Ser Lys Asn Gln Phe Ser Leu Arg Leu Ser Ser Val Thr Ala Ala Asp
    355                 360                 365 acc gcg gtt tat tat tgt gca aga tcc cta gct cgg act acg gct atg    1152
Thr Ala Val Tyr Tyr Cys Ala Arg Ser Leu Ala Arg Thr Thr Ala Met
370                 375                 380 gac tac tgg ggt caa ggc agc ctc gtc aca gtc tcc tca ggt ggt ggt    1200
Asp Tyr Trp Gly Gln Gly Ser Leu Val Thr Val Ser Ser Gly Gly Gly
385                 390                 395                 400 ggt tcg ggt ggt ggt ggt tcg ggt ggt ggc gga tcg gac atc cag atg    1248
Gly Ser Gly Gly Gly Gly Ser Gly Gly Gly Gly Ser Asp Ile Gln Met
            405                 410                 415 acc cag agc cca agc agc ctg agc gcc agc gtg ggt gac aga gtg acc    1296
Thr Gln Ser Pro Ser Ser Leu Ser Ala Ser Val Gly Asp Arg Val Thr
                420                 425                 430 atc acc tgt aga gcc agc cag gac atc agc agt tac ctg aat tgg tac    1344
Ile Thr Cys Arg Ala Ser Gln Asp Ile Ser Ser Tyr Leu Asn Trp Tyr
        435                 440                 445 cag cag aag cca gga aag gct cca aag ctg ctg atc tac tac acc tcc    1392
Gln Gln Lys Pro Gly Lys Ala Pro Lys Leu Leu Ile Tyr Tyr Thr Ser
    450                 455                 460 aga ctg cac tct ggt gtg cca agc aga ttc agc ggt agc ggt agc ggt    1440
Arg Leu His Ser Gly Val Pro Ser Arg Phe Ser Gly Ser Gly Ser Gly
465                 470                 475                 480 acc gac ttc acc ttc acc atc agc agc ctc cag cca gag gac atc gct    1488
Thr Asp Phe Thr Phe Thr Ile Ser Ser Leu Gln Pro Glu Asp Ile Ala
                485                 490                 495 acc tac tac tgc caa cag gga aat act tta cca tac acg ttc ggc caa    1536
Thr Tyr Tyr Cys Gln Gln Gly Asn Thr Leu Pro Tyr Thr Phe Gly Gln
                500                 505                 510 ggg acc aag gtg gaa atc aaa                                        1557
Gly Thr Lys Val Glu Ile Lys
        515
```

<210> SEQ ID NO 31
<211> LENGTH: 29
<212> TYPE: DNA
<213> ORGANISM: Artificial Sequence
<220> FEATURE:
<223> OTHER INFORMATION: Description of Artificial Sequence: "Kappa1",
      an artificially synthesized primer sequence
<400> SEQUENCE: 31
ccgccatctg atgagcagtt gaaatctgg                                29

<210> SEQ ID NO 32
<211> LENGTH: 54
<212> TYPE: DNA
<213> ORGANISM: Artificial Sequence
<220> FEATURE:
<223> OTHER INFORMATION: Description of Artificial Sequence: "Kappa2",
      an artificially synthesized primer sequence
<400> SEQUENCE: 32
ttatttatcg tcatcgtctt tgtagtcaag cttagactct ccctgttga agct        54

<210> SEQ ID NO 33
<211> LENGTH: 29
<212> TYPE: DNA
<213> ORGANISM: Artificial Sequence
<220> FEATURE:
<223> OTHER INFORMATION: Description of Artificial Sequence: "SCP-K",
      an artificially synthesized primer sequence
<400> SEQUENCE: 33
ttcaactgct catcagatgg cgggaagat                                29

<210> SEQ ID NO 34
<211> LENGTH: 1878
<212> TYPE: DNA
<213> ORGANISM: Artificial Sequence
<220> FEATURE:
<221> NAME/KEY: CDS
<222> LOCATION: (1)..(1878)
<220> FEATURE:
<223> OTHER INFORMATION: Description of Artificial Sequence:
"shPM1-Kappa-BvGS3", a designed single chain Fv gene sequence

<400> SEQUENCE: 34

| | | | | | | | | | | | | | | | | |
|---|---|---|---|---|---|---|---|---|---|---|---|---|---|---|---|---|
| atg | gga | tgg | agc | tgt | atc | atc | ctc | ttc | ttg | gta | gca | aca | gct | aca | ggt | 48 |
| Met | Gly | Trp | Ser | Cys | Ile | Ile | Leu | Phe | Leu | Val | Ala | Thr | Ala | Thr | Gly | |
| 1 | | | | 5 | | | | | 10 | | | | | 15 | | |
| gtc | gac | tcc | cag | gtc | caa | ctg | cag | gag | agc | ggt | cca | ggt | ctt | gtg | aga | 96 |
| Val | Asp | Ser | Gln | Val | Gln | Leu | Gln | Glu | Ser | Gly | Pro | Gly | Leu | Val | Arg | |
| | | | 20 | | | | | 25 | | | | | 30 | | | |
| cct | agc | cag | acc | ctg | agc | ctg | acc | tgc | acc | gtg | tct | ggc | tac | tca | att | 144 |
| Pro | Ser | Gln | Thr | Leu | Ser | Leu | Thr | Cys | Thr | Val | Ser | Gly | Tyr | Ser | Ile | |
| | | 35 | | | | | 40 | | | | | 45 | | | | |
| acc | agc | gat | cat | gcc | tgg | agc | tgg | gtt | cgc | cag | cca | cct | gga | cga | ggt | 192 |
| Thr | Ser | Asp | His | Ala | Trp | Ser | Trp | Val | Arg | Gln | Pro | Pro | Gly | Arg | Gly | |
| | 50 | | | | | 55 | | | | | 60 | | | | | |
| ctt | gag | tgg | att | gga | tac | att | agt | tat | agt | gga | atc | aca | acc | tat | aat | 240 |
| Leu | Glu | Trp | Ile | Gly | Tyr | Ile | Ser | Tyr | Ser | Gly | Ile | Thr | Thr | Tyr | Asn | |
| 65 | | | | | 70 | | | | | 75 | | | | | 80 | |
| cca | tct | ctc | aaa | tcc | aga | gtg | aca | atg | ctg | aga | gac | acc | agc | aag | aac | 288 |
| Pro | Ser | Leu | Lys | Ser | Arg | Val | Thr | Met | Leu | Arg | Asp | Thr | Ser | Lys | Asn | |
| | | | | 85 | | | | | 90 | | | | | 95 | | |
| cag | ttc | agc | ctg | aga | ctc | agc | agc | gtg | aca | gcc | gcc | gac | acc | gcg | gtt | 336 |
| Gln | Phe | Ser | Leu | Arg | Leu | Ser | Ser | Val | Thr | Ala | Ala | Asp | Thr | Ala | Val | |
| | | | 100 | | | | | 105 | | | | | 110 | | | |
| tat | tat | tgt | gca | aga | tcc | cta | gct | cgg | act | acg | gct | atg | gac | tac | tgg | 384 |
| Tyr | Tyr | Cys | Ala | Arg | Ser | Leu | Ala | Arg | Thr | Thr | Ala | Met | Asp | Tyr | Trp | |
| | | 115 | | | | | 120 | | | | | 125 | | | | |
| ggt | caa | ggc | agc | ctc | gtc | aca | gtc | tcc | tca | ggt | ggt | ggt | ggt | tcg | ggt | 432 |
| Gly | Gln | Gly | Ser | Leu | Val | Thr | Val | Ser | Ser | Gly | Gly | Gly | Gly | Ser | Gly | |
| | 130 | | | | | 135 | | | | | 140 | | | | | |
| ggt | ggt | ggt | tcg | ggt | ggt | ggc | gga | tcg | gac | atc | cag | atg | acc | cag | agc | 480 |
| Gly | Gly | Gly | Ser | Gly | Gly | Gly | Gly | Ser | Asp | Ile | Gln | Met | Thr | Gln | Ser | |
| 145 | | | | | 150 | | | | | 155 | | | | | 160 | |
| cca | agc | agc | ctg | agc | gcc | agc | gtg | ggt | gac | aga | gtg | acc | atc | acc | tgt | 528 |
| Pro | Ser | Ser | Leu | Ser | Ala | Ser | Val | Gly | Asp | Arg | Val | Thr | Ile | Thr | Cys | |
| | | | | 165 | | | | | 170 | | | | | 175 | | |
| aga | gcc | agc | cag | gac | atc | agc | agt | tac | ctg | aat | tgg | tac | cag | cag | aag | 576 |
| Arg | Ala | Ser | Gln | Asp | Ile | Ser | Ser | Tyr | Leu | Asn | Trp | Tyr | Gln | Gln | Lys | |
| | | | 180 | | | | | 185 | | | | | 190 | | | |
| cca | gga | aag | gct | cca | aag | ctg | ctg | atc | tac | tac | acc | tcc | aga | ctg | cac | 624 |
| Pro | Gly | Lys | Ala | Pro | Lys | Leu | Leu | Ile | Tyr | Tyr | Thr | Ser | Arg | Leu | His | |
| | | 195 | | | | | 200 | | | | | 205 | | | | |
| tct | ggt | gtg | cca | agc | aga | ttc | agc | ggt | agc | ggt | agc | ggt | acc | gac | ttc | 672 |
| Ser | Gly | Val | Pro | Ser | Arg | Phe | Ser | Gly | Ser | Gly | Ser | Gly | Thr | Asp | Phe | |
| | 210 | | | | | 215 | | | | | 220 | | | | | |
| acc | ttc | acc | atc | agc | agc | ctc | cag | cca | gag | gac | atc | gct | acc | tac | tac | 720 |
| Thr | Phe | Thr | Ile | Ser | Ser | Leu | Gln | Pro | Glu | Asp | Ile | Ala | Thr | Tyr | Tyr | |
| 225 | | | | | 230 | | | | | 235 | | | | | 240 | |
| tgc | caa | cag | ggt | aac | acg | ctt | cca | tac | acg | ttc | ggc | caa | ggg | acc | aag | 768 |
| Cys | Gln | Gln | Gly | Asn | Thr | Leu | Pro | Tyr | Thr | Phe | Gly | Gln | Gly | Thr | Lys | |
| | | | | 245 | | | | | 250 | | | | | 255 | | |
| gtg | gaa | atc | aaa | ggt | ggt | ggt | ggt | tcg | ggt | ggt | ggt | ggt | tcg | ggt | ggt | 816 |

```
                Val Glu Ile Lys Gly Gly Gly Ser Gly Gly Gly Ser Gly Gly
                                260             265             270 ggc gga tcg gtc gac tcc cag gtc caa ctg cag gag agc ggt cca ggt      864
Gly Gly Ser Val Asp Ser Gln Val Gln Leu Gln Glu Ser Gly Pro Gly
                275             280             285 ctt gtg aga cct agc cag acc ctg agc ctg acc tgc acc gtg tct ggc      912
Leu Val Arg Pro Ser Gln Thr Leu Ser Leu Thr Cys Thr Val Ser Gly
            290             295             300 tac tca att acc agc gat cat gcc tgg agc tgg gtt cgc cag cca cct      960
Tyr Ser Ile Thr Ser Asp His Ala Trp Ser Trp Val Arg Gln Pro Pro
305             310             315             320 gga cga ggt ctt gag tgg att gga tac att agt tat agt gga atc aca     1008
Gly Arg Gly Leu Glu Trp Ile Gly Tyr Ile Ser Tyr Ser Gly Ile Thr
                325             330             335 acc tat aat cca tct ctc aaa tcc aga gtg aca atg ctg aga gac acc     1056
Thr Tyr Asn Pro Ser Leu Lys Ser Arg Val Thr Met Leu Arg Asp Thr
            340             345             350 agc aag aac cag ttc agc ctg aga ctc agc agc gtg aca gcc gcc gac     1104
Ser Lys Asn Gln Phe Ser Leu Arg Leu Ser Ser Val Thr Ala Ala Asp
        355             360             365 acc gcg gtt tat tat tgt gca aga tcc cta gct cgg act acg gct atg     1152
Thr Ala Val Tyr Tyr Cys Ala Arg Ser Leu Ala Arg Thr Thr Ala Met
    370             375             380 gac tac tgg ggt caa ggc agc ctc gtc aca gtc tcc tca ggt ggt ggt     1200
Asp Tyr Trp Gly Gln Gly Ser Leu Val Thr Val Ser Ser Gly Gly Gly
385             390             395             400 ggt tcg ggt ggt ggt ggt tcg ggt ggt ggc gga tcg gac atc cag atg     1248
Gly Ser Gly Gly Gly Gly Ser Gly Gly Gly Gly Ser Asp Ile Gln Met
                405             410             415 acc cag agc cca agc agc ctg agc gcc agc gtg ggt gac aga gtg acc     1296
Thr Gln Ser Pro Ser Ser Leu Ser Ala Ser Val Gly Asp Arg Val Thr
            420             425             430 atc acc tgt aga gcc agc cag gac atc agc agt tac ctg aat tgg tac     1344
Ile Thr Cys Arg Ala Ser Gln Asp Ile Ser Ser Tyr Leu Asn Trp Tyr
        435             440             445 cag cag aag cca gga aag gct cca aag ctg ctg atc tac tac acc tcc     1392
Gln Gln Lys Pro Gly Lys Ala Pro Lys Leu Leu Ile Tyr Tyr Thr Ser
    450             455             460 aga ctg cac tct ggt gtg cca agc aga ttc agc ggt agc ggt agc ggt     1440
Arg Leu His Ser Gly Val Pro Ser Arg Phe Ser Gly Ser Gly Ser Gly
465             470             475             480 acc gac ttc acc ttc acc atc agc agc ctc cag cca gag gac atc gct     1488
Thr Asp Phe Thr Phe Thr Ile Ser Ser Leu Gln Pro Glu Asp Ile Ala
                485             490             495 acc tac tac tgc caa cag gga aat act tta cca tac acg ttc ggc caa     1536
Thr Tyr Tyr Cys Gln Gln Gly Asn Thr Leu Pro Tyr Thr Phe Gly Gln
            500             505             510 ggg acc aag gtg gaa atc aaa cga act gtg gct gca cca tct gtc ttc     1584
Gly Thr Lys Val Glu Ile Lys Arg Thr Val Ala Ala Pro Ser Val Phe
        515             520             525 atc ttc ccg cca tct gat gag cag ttg aaa tct gga act gcc tct gtt     1632
Ile Phe Pro Pro Ser Asp Glu Gln Leu Lys Ser Gly Thr Ala Ser Val
    530             535             540 gtg tgc ctg ctg aat aac ttc tat ccc aga gag gcc aaa gta cag tgg     1680
Val Cys Leu Leu Asn Asn Phe Tyr Pro Arg Glu Ala Lys Val Gln Trp
545             550             555             560 aag gtg gat aac gcc ctc caa tcg ggt aac tcc cag gag agt gtc aca     1728
Lys Val Asp Asn Ala Leu Gln Ser Gly Asn Ser Gln Glu Ser Val Thr
                565             570             575
```

| gag cag gac agc aag gac agc acc tac agc ctc agc agc acc ctg acg | 1776 |
| Glu Gln Asp Ser Lys Asp Ser Thr Tyr Ser Leu Ser Ser Thr Leu Thr | |
| 580 585 590 | |

| ctg agc aaa gca gac tac gag aaa cac aaa gtc tac gcc tgc gaa gtc | 1824 |
| Leu Ser Lys Ala Asp Tyr Glu Lys His Lys Val Tyr Ala Cys Glu Val | |
| 595 600 605 | |

| acc cat cag ggc ctg agc tcg ccc gtc aca aag agc ttc aac agg gga | 1872 |
| Thr His Gln Gly Leu Ser Ser Pro Val Thr Lys Ser Phe Asn Arg Gly | |
| 610 615 620 | |

| gag tct | 1878 |
| Glu Ser | |
| 625 | |

<210> SEQ ID NO 35
<211> LENGTH: 29
<212> TYPE: DNA
<213> ORGANISM: Artificial Sequence
<220> FEATURE:
<223> OTHER INFORMATION: Description of Artificial Sequence: "MCH4-1",
  an artificially synthesized primer sequence
<400> SEQUENCE: 35
gtggaaatca aagtggccct gcacaggcc                              29

<210> SEQ ID NO 36
<211> LENGTH: 68
<212> TYPE: DNA
<213> ORGANISM: Artificial Sequence
<220> FEATURE:
<223> OTHER INFORMATION: Description of Artificial Sequence: "MCH4-2.1",
    an artificially synthesized primer sequence
<400> SEQUENCE: 36
tagtcaagct tctcaaatcc ctcttcgtcg gcgctaacct ctccttcggt ggacttgtcc    60
acggtcct                                                             68

<210> SEQ ID NO 37
<211> LENGTH: 29
<212> TYPE: DNA
<213> ORGANISM: Artificial Sequence
<220> FEATURE:
<223> OTHER INFORMATION: Description of Artificial Sequence: "SCP-Mu",
    an artificially synthesized primer sequence
<400> SEQUENCE: 37
tgcagggcca ctttgatttc caccttggt                              29

<210> SEQ ID NO 38
<211> LENGTH: 53
<212> TYPE: DNA
<213> ORGANISM: Artificial Sequence
<220> FEATURE:
<223> OTHER INFORMATION: Description of Artificial Sequence: "MCH4-2.2",
    an artificially synthesized primer sequence
<400> SEQUENCE: 38
aaagcggccg cttattattt atcgtcatcg tctttgtagt caagcttctc aaa    53

<210> SEQ ID NO 39
<211> LENGTH: 1920
<212> TYPE: DNA
<213> ORGANISM: Artificial Sequence
<220> FEATURE:
<221> NAME/KEY: CDS
<222> LOCATION: (1)..(1920)
<220> FEATURE:
<223> OTHER INFORMATION: Description of Artificial Sequence:
    "shPM1-MCH-BvGS3", a designed single chain Fv gene sequence
<400> SEQUENCE: 39

```
atg gga tgg agc tgt atc atc ctc ttc ttg gta gca aca gct aca ggt        48
Met Gly Trp Ser Cys Ile Ile Leu Phe Leu Val Ala Thr Ala Thr Gly
 1               5                  10                 15 gtc gac tcc cag gtc caa ctg cag gag agc ggt cca ggt ctt gtg aga        96
Val Asp Ser Gln Val Gln Leu Gln Glu Ser Gly Pro Gly Leu Val Arg
             20                 25                  30 cct agc cag acc ctg agc ctg acc tgc acc gtg tct ggc tac tca att       144
Pro Ser Gln Thr Leu Ser Leu Thr Cys Thr Val Ser Gly Tyr Ser Ile
         35                  40                  45 acc agc gat cat gcc tgg agc tgg gtt cgc cag cca cct gga cga ggt       192
Thr Ser Asp His Ala Trp Ser Trp Val Arg Gln Pro Pro Gly Arg Gly
     50                  55                  60 ctt gag tgg att gga tac att agt tat agt gga atc aca acc tat aat       240
Leu Glu Trp Ile Gly Tyr Ile Ser Tyr Ser Gly Ile Thr Thr Tyr Asn
 65                  70                  75                  80 cca tct ctc aaa tcc aga gtg aca atg ctg aga gac acc agc aag aac       288
Pro Ser Leu Lys Ser Arg Val Thr Met Leu Arg Asp Thr Ser Lys Asn
                 85                  90                  95 cag ttc agc ctg aga ctc agc agc gtg aca gcc gcc gac acc gcg gtt       336
Gln Phe Ser Leu Arg Leu Ser Ser Val Thr Ala Ala Asp Thr Ala Val
            100                 105                 110 tat tat tgt gca aga tcc cta gct cgg act acg gct atg gac tac tgg       384
Tyr Tyr Cys Ala Arg Ser Leu Ala Arg Thr Thr Ala Met Asp Tyr Trp
        115                 120                 125 ggt caa ggc agc ctc gtc aca gtc tcc tca ggt ggt ggt ggt tcg ggt       432
Gly Gln Gly Ser Leu Val Thr Val Ser Ser Gly Gly Gly Gly Ser Gly
130                 135                 140 ggt ggt ggt tcg ggt ggt ggc gga tcg gac atc cag atg acc cag agc       480
Gly Gly Gly Ser Gly Gly Gly Gly Ser Asp Ile Gln Met Thr Gln Ser
145                 150                 155                 160 cca agc agc ctg agc gcc agc gtg ggt gac aga gtg acc atc acc tgt       528
Pro Ser Ser Leu Ser Ala Ser Val Gly Asp Arg Val Thr Ile Thr Cys
                165                 170                 175 aga gcc agc cag gac atc agc agt tac ctg aat tgg tac cag cag aag       576
Arg Ala Ser Gln Asp Ile Ser Ser Tyr Leu Asn Trp Tyr Gln Gln Lys
            180                 185                 190 cca gga aag gct cca aag ctg ctg atc tac tac acc tcc aga ctg cac       624
Pro Gly Lys Ala Pro Lys Leu Leu Ile Tyr Tyr Thr Ser Arg Leu His
        195                 200                 205 tct ggt gtg cca agc aga ttc agc ggt agc ggt agc ggt acc gac ttc       672
Ser Gly Val Pro Ser Arg Phe Ser Gly Ser Gly Ser Gly Thr Asp Phe
210                 215                 220 acc ttc acc atc agc agc ctc cag cca gag gac atc gct acc tac tac       720
Thr Phe Thr Ile Ser Ser Leu Gln Pro Glu Asp Ile Ala Thr Tyr Tyr
225                 230                 235                 240 tgc caa cag ggt aac acg ctt cca tac acg ttc ggc caa ggg acc aag       768
Cys Gln Gln Gly Asn Thr Leu Pro Tyr Thr Phe Gly Gln Gly Thr Lys
                245                 250                 255 gtg gaa atc aaa ggt ggt ggt ggt tcg ggt ggt ggt ggt tcg ggt ggt       816
Val Glu Ile Lys Gly Gly Gly Gly Ser Gly Gly Gly Gly Ser Gly Gly
            260                 265                 270 ggc gga tcg gtc gac tcc cag gtc caa ctg cag gag agc ggt cca ggt       864
Gly Gly Ser Val Asp Ser Gln Val Gln Leu Gln Glu Ser Gly Pro Gly
        275                 280                 285 ctt gtg aga cct agc cag acc ctg agc ctg acc tgc acc gtg tct ggc       912
Leu Val Arg Pro Ser Gln Thr Leu Ser Leu Thr Cys Thr Val Ser Gly
        290                 295                 300 tac tca att acc agc gat cat gcc tgg agc tgg gtt cgc cag cca cct       960
Tyr Ser Ile Thr Ser Asp His Ala Trp Ser Trp Val Arg Gln Pro Pro
305                 310                 315                 320
```

-continued

```
gga cga ggt ctt gag tgg att gga tac att agt tat agt gga atc aca    1008
Gly Arg Gly Leu Glu Trp Ile Gly Tyr Ile Ser Tyr Ser Gly Ile Thr
            325                 330                 335 acc tat aat cca tct ctc aaa tcc aga gtg aca atg ctg aga gac acc    1056
Thr Tyr Asn Pro Ser Leu Lys Ser Arg Val Thr Met Leu Arg Asp Thr
            340                 345                 350 agc aag aac cag ttc agc ctg aga ctc agc agc gtg aca gcc gcc gac    1104
Ser Lys Asn Gln Phe Ser Leu Arg Leu Ser Ser Val Thr Ala Ala Asp
            355                 360                 365 acc gcg gtt tat tat tgt gca aga tcc cta gct cgg act acg gct atg    1152
Thr Ala Val Tyr Tyr Cys Ala Arg Ser Leu Ala Arg Thr Thr Ala Met
    370                 375                 380 gac tac tgg ggt caa ggc agc ctc gtc aca gtc tcc tca ggt ggt ggt    1200
Asp Tyr Trp Gly Gln Gly Ser Leu Val Thr Val Ser Ser Gly Gly Gly
385                 390                 395                 400 ggt tcg ggt ggt ggt ggt tcg ggt ggt ggc gga tcg gac atc cag atg    1248
Gly Ser Gly Gly Gly Gly Ser Gly Gly Gly Gly Ser Asp Ile Gln Met
                405                 410                 415 acc cag agc cca agc agc ctg agc gcc agc gtg ggt gac aga gtg acc    1296
Thr Gln Ser Pro Ser Ser Leu Ser Ala Ser Val Gly Asp Arg Val Thr
            420                 425                 430 atc acc tgt aga gcc agc cag gac atc agc agt tac ctg aat tgg tac    1344
Ile Thr Cys Arg Ala Ser Gln Asp Ile Ser Ser Tyr Leu Asn Trp Tyr
            435                 440                 445 cag cag aag cca gga aag gct cca aag ctg ctg atc tac tac acc tcc    1392
Gln Gln Lys Pro Gly Lys Ala Pro Lys Leu Leu Ile Tyr Tyr Thr Ser
    450                 455                 460 aga ctg cac tct ggt gtg cca agc aga ttc agc ggt agc ggt agc ggt    1440
Arg Leu His Ser Gly Val Pro Ser Arg Phe Ser Gly Ser Gly Ser Gly
465                 470                 475                 480 acc gac ttc acc ttc acc atc agc agc ctc cag cca gag gac atc gct    1488
Thr Asp Phe Thr Phe Thr Ile Ser Ser Leu Gln Pro Glu Asp Ile Ala
                485                 490                 495 acc tac tac tgc caa cag gga aat act tta cca tac acg ttc ggc caa    1536
Thr Tyr Tyr Cys Gln Gln Gly Asn Thr Leu Pro Tyr Thr Phe Gly Gln
            500                 505                 510 ggg acc aag gtg gaa atc aaa gtg gcc ctg cac agg ccc gat gtc tac    1584
Gly Thr Lys Val Glu Ile Lys Val Ala Leu His Arg Pro Asp Val Tyr
            515                 520                 525 ttg ctg cca cca gcc cgg gag cag ctg aac ctg cgc gag tcg gcc acc    1632
Leu Leu Pro Pro Ala Arg Glu Gln Leu Asn Leu Arg Glu Ser Ala Thr
    530                 535                 540 atc acg tgc ctg gtg acg ggc ttc tct ccc gcg gac gtc ttc gtg cag    1680
Ile Thr Cys Leu Val Thr Gly Phe Ser Pro Ala Asp Val Phe Val Gln
545                 550                 555                 560 tgg atg cag agg ggg cag ccc ttg tcc ccg gag aag tat gtg acc agc    1728
Trp Met Gln Arg Gly Gln Pro Leu Ser Pro Glu Lys Tyr Val Thr Ser
                565                 570                 575 gcc cca atg cct gag ccc cag gcc cca ggc cgg tac ttc gcc cac agc    1776
Ala Pro Met Pro Glu Pro Gln Ala Pro Gly Arg Tyr Phe Ala His Ser
            580                 585                 590 atc ctg acc gtg tcc gaa gag gaa tgg aac acg ggg gag acc tac acc    1824
Ile Leu Thr Val Ser Glu Glu Glu Trp Asn Thr Gly Glu Thr Tyr Thr
            595                 600                 605 tgc gtg gcc cat gag gcc ctg ccc aac agg gtc acc gag agg acc gtg    1872
Cys Val Ala His Glu Ala Leu Pro Asn Arg Val Thr Glu Arg Thr Val
    610                 615                 620
```

```
                                                    -continued
gac aag tcc acc gag ggg gag gtg agc gcc gac gag gag ggc ttt gag         1920
Asp Lys Ser Thr Glu Gly Glu Val Ser Ala Asp Glu Glu Gly Phe Glu
625             630             635             640
```

METHODS FOR ISOLATING A CDNA ENCODING A MEMBRANE-BOUND PROTEIN

TECHNICAL FIELD

The present invention relates to a novel gene-cloning-method for selectively and efficiently isolating genes encoding membrane-bound proteins.

BACKGROUND ART

Proteins synthesized in cells can be categorized by their individual characteristics into those localized in intracellular organelles, such as nucleus, mitochondria, cytoplasm, etc.; those that function by binding to the cell membrane, such as receptors and channeling molecules; and those that function by being secreted to the cell exterior, such as growth factors and cytokines, etc. In particular, protein molecules bound to the cell membrane are responsible for biologically important functions, such as cellular responses towards growth factors and differentiation factors, inflammatory responses, cell-cell interactions, hormone responses, and so on, and therefore, can be target molecules for diagnostic and therapeutic drugs for various types of disorders.

In recent years, as typified by the genome-project, mass gene-cloning-methods employing random approaches are being conducted, and enormous gene sequence information such as large amounts of ESTs (Expressed Sequence Tags) are accumulated (Matsubara, K. Artificial Organs (1996) 20, 823–827). However, the identification of a protein having a desired function from these ESTs is by no means an easy task, and in order to predict and analyze the function of an encoded-protein from gene sequence information, a great deal of time and efforts are required. Therefore, a method to select, at least upto a certain extent, a gene encoding a protein expected to have a desired function at the stage of random cDNA cloning has been long awaited.

Cloning methods utilizing protein localization were developed as a solution to such problems. For example, proteins secreted to the cell exterior have an amino acid sequence comprising 15 to 30 or so amino acid residues vital for secretion, which is generally termed as a secretion signal sequence or a leader sequence.

Tashiro, K. et al. focused their attention on the features of this secretory protein synthesis and developed a cloning method that specifically selects a gene encoding a secretory protein (Tashiro, K. et al., Science (1993) 261, 300–603). When the signal sequence of proteins that are normally secreted to the cell exterior, for example, interleukin-2 (IL-2) receptor, is deleted, they are unable to express on the cell membrane. If the cDNA encoding the secretion signal sequence is fused, this IL-2 receptor can be re-expressed on the cell membrane as a fusion protein. Since IL-2 receptor fusion protein-expressing cells can be selected by an antibody recognizing the IL-2 receptor, cDNA encoding the protein of which the signal sequence introduced to cells have functioned can be isolated. This method is generally called the SST (Signal Sequence Trap) method as it selectively clones a gene encoding a signal sequence. A cloning method for yeasts has also been developed by basically the same principle (U.S. Pat. No. 5,536,637).

However, even if a gene fragment encoding a protein comprising a signal sequence is obtained by this method, one cannot know whether it is a secretory protein, or whether it is a membrane-bound protein. Also, this method requires the utilization of a cDNA library comprising a 5' end, but techniques for efficiently constructing a cDNA library that selectively contains a 5' end are not necessarily easy, versatile techniques.

Recently, Ishihara et al. and Nakauchi et al. reported the TMT (Transmembrane Trap) method, which more selectively clones a gene encoding a membrane-bound protein (Yoshikazu Ichihara and Yoshikazu Kurozawa, Abstracts from the Annual Meeting of the Molecular Biology Society of Japan (1998), No. 3-509-P-533, Nakauchi et al. WO98/03645). The method of Ichihara et al. is based on a principle opposite to the above-mentioned SST method. Namely, the extracellular region of the IL-2 receptor and a protein containing the cell membrane-bound region encoded by cDNA are fused, the IL-2 receptor is expressed on cell membrane surface, and the cells are selected using an antibody against the IL-2 receptor. A model experiment of this method confirmed the expression of fusion molecules between type I or type II membrane-bound proteins, or glycosylphosphatidylinositol (GPI) anchor-type membrane-bound protein and IL-2 receptor on the cell membrane using the anti-IL-2 receptor antibody.

However, when the cDNA library was introduced, proteins not comprising the transmembrane region and membrane-bound region were also obtained within the selected cDNA. In other words, the cloning selectivity of the gene encoding the membrane-bound protein obtained by this TMT method is not necessarily high. This shows, for example, that although all fusion proteins not having the transmembrane region and GPI anchor should be secreted in principle, non-specific agglutinations not owing to the transmembrane region and GPI anchor may also occur on the cell membrane depending on the structures and amino acids compositions of the fusion proteins.

Furthermore, in the case of this TMT method, an epitope recognized by the antibody is expressed in the fusion protein. Therefore, even if fusion proteins expressed in the above manner are non-specifically adsorbed onto the cell membrane, the antibody will recognize and bind to the epitope as long as the epitope is exposed. Also, those molecules on the membrane surface that are on their way to being secreted to the cell exterior are also recognized by the antibody. Therefore, it is desired that the selectivity of membrane-bound protein-expressing cells obtained by this TMT method be further improved.

DISCLOSURE OF THE INVENTION

The present invention solves the problems of the TMT method and provides a gene cloning method with a superior selectivity.

A feature of the present invention is to isolate a gene encoding a membrane-bound protein by linking a functional protein to the fusion protein itself, differing from the conventional TMT method that carries an epitope recognizing an antibody. The present method thus enabled the selective isolation of genes encoding membrane-bound proteins.

Namely, the present invention provides:
 (1) a method for isolating a gene encoding a membrane-bound protein, the method comprising the steps of
  (i) introducing into cells a vector comprising a DNA comprising a DNA encoding a secretable, functional protein having a binding affinity to an antigen and a cDNA ligated downstream of the 3' side of the functional protein-encoding DNA,
  (ii) expressing within cells, the fusion protein of the secretable, functional protein.having a binding affinity to the antigen and the protein encoded by the cDNA, (iii) selecting cells binding to the antigen by contacting cells expressing the fusion protein on the cell membrane with an antigen, and (iv) isolating cDNA inserted within the vector from the selected cells, (2) the method of (1), wherein the vector introduced into cells in step (i) is obtained by introducing cDNA into a vector at the restriction enzyme site downstream of the 3' side of the functional protein-encoding DNA, (3) the method of (1), wherein the vector introduced into cells in step (i) is obtained by introducing into a vector, a DNA comprising a DNA encoding a functional protein and a cDNA ligated downstream of the 3, side of the functional protein-encoding DNA, (4) the method of any one of (1) to (3), wherein the DNA encoding the functional protein and the cDNA downstream of the 3' side thereof are ligated via a DNA encoding a peptide linker, (5) the method of any one of (1) to (4), wherein the cDNA is derived from a cDNA library obtained from mammalian cells, (6) the method of any one of (1) to (5), wherein the vector introduced into cells in the step (i) comprises a DNA encoding a secretion signal sequence upstream of the 5' side of the DNA encoding a functional protein, (7) the method of any one of (1) to (6), wherein the functional protein is an antibody, (8) the method of any one of (1) to (7), wherein the functional protein having a binding affinity to the antigen is a single-chain antibody, which is preferably monovalent or bivalent, (9) the method of any one of (1) to (8), wherein the vector contains a DNA in which a DNA encoding the constant region of the antibody is ligated downstream of the 3' side of the DNA encoding a single-chain antibody,

(10) the method of any one of (1) to (9), wherein the antigen is bound to a supporter,

(11) the method of (10), wherein the supporter is for cell-culturing,

(12) the method of any one of (1) to (11), comprising determining whether or not the gene obtained from cells comprises a novel sequence,

(13) the method of (12) comprising screening a cDNA library to obtain the full-length gene of the gene obtained from cells, the gene comprising a novel sequence,

(14) the method of (13) comprising isolating the full-length gene of the gene obtained from cells, the gene comprising a novel sequence,

(15) a kit for isolating a gene encoding a membrane-bound protein, the kit comprising a vector having a restriction enzyme recognition site for inserting a cDNA downstream of the 3' side of a DNA encoding a secretable, functional protein having a binding affinity to an antigen, and,

(16) the kit of (15) further comprising a supporter to which an antigen is bound and/or cells into which a vector is to be introduced.

As membrane-bound proteins isolatable by the method of the invention, for example, type I or type II membrane-bound proteins and GPI anchor-type membrane-bound proteins and such can be given. Type I or type II membrane-bound proteins are proteins comprising transmembrane regions, and bind to the membrane after being secreted to the cell exterior from N terminal side or C terminal side of the expressed polypeptides. Transmembrane regions are regions that penetrate the inside and the outside of the cell membrane, and because this transmembrane region remains in the cell membrane, proteins exist as being fixed onto the cell membrane. The transmembrane region is generally constituted of hydrophobic amino acid residue-rich regions within the amino acid sequence of the protein. A commercially available computer program, for example, the GCG Sequence Analysis Software Package (Genetic Computer Group, Oxford Molecular Group, Inc.) can easily predict whether a protein has a transmembrane region or not. GPI anchor type membrane-bound proteins are proteins that undergo modifications by GPI and that are anchored to the lipid layer of the cell membrane via GPI (GPI anchor type membrane-bound proteins).

In the first step ((i)) of the isolation method of the invention, a vector comprising a DNA encoding a secretable, functional protein having a binding affinity to an antigen and a DNA wherein a cDNA is ligated downstream of the 3' side thereof, is introduced into cells.

"A functional protein having binding affinity to an antigen" means a protein that can functionally bind to a certain antigen. As functional proteins, those of which the binding constant with the antigen is $10^7$M or more are preferable. It is more preferably $10^8$M or more, and is even more preferably $10^9$M or more. Functional proteins are, specifically, antibodies, antibody fragments, single-chain antibodies, etc. Antibodies comprise two heavy chains (H chain) and two light chains (L chain), and these H chains and L chains bind via disulfide bonds to make a single antibody molecule. H chain and L chain are composed of a variable region (v region, Fv) and a constant region (C region, Fc). Antibody fragments are partial proteins of antibodies having a binding affinity to antigens, and, for example, Fab, F(ab')2, Fv and such can be given. A single-chain antibody (hereafter called, single-chain Fv (scFv)), is a protein having binding affinity to an antigen, the protein in which the H chain Fv and L chain Fv are ligated by a linker, and, for example, a monovalent single-chain antibody and a bivalent single-chain antibody can be given. Monovalent single-chain antibodies have an antigen-binding site comprising one H chain Fv and L chain Fv, and bivalent single-chain antibodies have a structure in which two monovalent single-chain antibody molecules are ligated via a linker, and have two antigen-binding sites.

Antibodies, antibody fragments, or single-chain antibodies may be those wherein one or more amino acid residues have been deleted, inserted, and/or replaced with other amino acid residues for various purposes, such as improving the binding constant, or those which are fused with other peptides or polypeptides, and both are encompassed in the functional protein of the present invention. Also, modified antibodies may be used as the antibody, antibody fragment, or single-chain antibody. Examples of modified antibodies are chimeric antibodies and humanized antibodies. Chimeric antibodies are those comprising a V region and C region of antibodies derived from different animals. Humanized antibodies are those comprising complementarity determining region (CDR) of an antibody derived from an animal other than humans, and the framework region (FR) and the C region of an antibody derived from humans.

An antigen having binding affinity to the functional protein of the invention may be any substance as long as it has antigenicity. Examples are, proteins, peptides, and sugars and such, preferably proteins. Proteins used as antigens are, for example, cells or microorganisms expressing proteins, serum proteins, cytokines, intracellular proteins, membrane proteins, etc.

DNA encoding the antibody can be obtained by well-known means. Namely, they can be isolated from antibody-producing cells, for example, hybridoma, immortalized lymphocytes sensitized by an antigen, and cells producing a recombinant antibody following the introduction of an antibody gene. In addition, DNA that have been already isolated and inserted into a vector may also be used. The origin and type of the DNA encoding the antibody are not questioned as long as it can be used in the present invention.

DNA encoding an antibody fragment or single-chain antibody can be constructed from DNA encoding the antibody by following methods usually employed. DNA encoding a monovalent single-chain antibody is obtained by ligating DNA encoding the H chain V region (H chain Fv) of the antibody, DNA encoding the linker, and DNA encoding the L chain V region (L chain Fv). The linker is not restricted as long as it can sterically reproduce the H chain Fv and L chain Fv so that they have an antigen affinity. Preferably it is a peptide linker and, for example, comprises 12 to 19 amino acid residues (Huston, J. S. et al., Proc. Natl. Acad. Sci. U.S.A. (1988) 85, 5879–5883). Specifically, a peptide linker having the following amino acid sequence can be given: GlyGlyGlyGlySerGlyGlyGlyGly-SerGlyGlyGlyGlySer (($Gly_4Ser$)$_3$) (SEQ ID NO: 1). DNA encoding a bivalent single-chain antibody is constructed by linking the 5' end and 3' end of two DNA molecules encoding a monovalent single-chain antibody using a DNA encoding a peptide linker. The peptide linker ligating two single-chain antibodies comprises, for example, the amino acid sequence of GlyGlyGlyGlySerGlyGlyGlyGly-SerGlyGlyGlyGlySer (($Gly_4Ser$)$_3$) (SEQ ID NO: 1).

In order to increase the cloning efficiency in the invention, for example, when using single-chain Fv as the functional protein, it is preferable that the C terminus contains a small amount of hydrophobic amino acids, and specifically, a single-chain Fv in which the elbow region has been deleted as described in Examples below can be used. Also, it is preferable that, in the present invention, stability and expression efficiency can be increased by ligating further a domain of secretory protein origin, for example, a DNA encoding amino acids of the constant region of an antibody described in Examples below, to the C terminus of single-chain Fv.

For a functional protein to be secretable, a secretion signal sequence can be used. Namely, it is enough to ligate a DNA encoding a secretion signal sequence upstream of the 5' side of a DNA encoding a functional protein having a binding affinity to an antigen. As a secretion signal sequence, one that is suitable for cells used for the expression of a cDNA library and the secretion of proteins, is employed. The secretion signal sequence may be a signal sequence of any secretory protein as long as it can secrete the functional protein. Preferable animal-derived secretion signal sequences are those deriving from mammals, for example, the signal sequence of human immunoglobulin (Kabat, E. et al., Sequences of Proteins of Immunological Interest, US Department of Health and Human Services (1991)), of cytokines, and of cytokine receptors.

cDNA ligated downstream of the 3' side of a DNA encoding the functional protein preferably derives from a cDNA library. As the cDNA library, one obtained using well-known methods, or one that is commercially available may be used. A cDNA library can be prepared by isolating mRNA from desired samples and synthesizing cDNA from the isolated mRNA.

Sources from which mRNA could be isolated are, for example, mammals, animals other than mammals, plants, yeasts, bacteria, or blue-green algae, and preferably, mammals are used. Humans, monkeys, rabbits, rats, mice and such can be given as examples of mammals, and especially humans are preferable. Animals other than mammals are, for example, insects such as fruit flies (Drosophila), etc.

Sources from which mRNA could be isolated may be any sources, for example, cells obtained from a living body, established cell lines, embryos, tissues, blood, or organs. Representative examples are osteoblasts, hematopoietic stem cells, smooth muscle cells, neurons, stromal cells, ES cells, liver, intestine, lung, kidney, lymph nodes, etc.

Isolation of mRNA could be done by suspending the samples for isolation under the presence of a commonly used buffer by commonly used methods. To prepare whole mRNA as the first step of mRNA isolation, for example, the guanosine ultracentrifugation method (Chirgwin, J. M. et al., Biochemistry (1979) 18, 5294–5299) or the AGPC method (Chomczynski, P. and Sacchi, N., Anal. Biochem. (1987) 162, 156–159) and such could be employed. Next, for purifying mRNA from the whole mRNA, for example, the mRNA Purification Kit (Pharmacia) and such could be used. For example, QuickPrep mRNA Purification Kit (Pharmacia) may also be used as a commercially available kit for concentrating mRNA through affinity purification using oligo dT.

cDNA is synthesized from the obtained mRNA using reverse transcriptase. Commercially available reverse transcriptase could be used. Single-stranded cDNA complementary to the mRNA could be synthesized by using an oligo dT primer complementary to the poly A of mRNA, or using an oligonucleotide of a random sequence as the primer. For example, the AMV Reverse Transcriptase First-strand cDNA Synthesis Kit (Seikagaku Corporation) and such may be utilized to synthesize cDNA. Double-stranded cDNA is prepared from the obtained single-stranded cDNA by DNA polymerase.

Furthermore, the cDNA library can also be selectively condensed for a specific purpose using commonly used methods. For a specific purpose, for example, for obtaining cDNA of a gene in which the expression amount varies, the differential cloning method (Lau, L. F. et al., and Nathans, D. EMBO J. (1985) 4, 3145–3151), the differential display method (Liang, P. and Pardee, A. B. Science (1992) 257, 967–971), the subtractive cloning method (Nucleic Acids Research (1988) 16, 10937), or the serial analysis gene expression method (SAGE method) (Velculescu, V. E. et al. Science (1995) 270, 484–487) may be utilized. The SST method (Tashiro, K. et al., Science (1993) 261, 300–603) and the method described in U.S. Pat. No. 5,536,637 may also be utilized to condense cDNA encoding a secretory protein.

Vectors may be any vectors as long as they can transform cells and express the DNA contained therein. It is preferable to select, as an expression vector, a vector that can operate in cells to be transformed. Examples of expression vectors are plasmid vectors and virus-derived vectors.

The obtained cDNA is ligated to a vector. At this instance, cDNA can be introduced into the vector by introducing it downstream of the 3' side of a functional protein encoding-DNA that is already contained in the vector. For this purpose, a suitable restriction enzyme site, for example, a multi-cloning site is designed downstream of the 3' side of the DNA encoding the functional protein, and the cDNA is introduced into that site. Also, cDNA may be ligated first downstream of the DNA encoding the functional protein, and then the obtained DNA may be introduced into the vector. The DNA construct can be introduced into a suitable restriction enzyme site comprised in a vector DNA. When preparing the vector, the DNA encoding the functional protein and the cDNA located downstream of the 3' side may be directly ligated, or may be ligated via a DNA encoding a peptide linker to enable easy binding of the functional protein to the antigen.

The expression vector preferably contains an expression-regulating region needed for the expression of a desired DNA in cells. Promoters/enhancers can be given as expression regulating regions, and specifically, the human EF1α promoter HCMV promoter, or SV40 promoter and such can be given. Expression vectors prepared in such a manner can be introduced into cells using commonly used methods. Examples of such methods are, the electroporation method (EMBO J. (1982) 1, 841–845), the calcium phosphate method (Virology (1973) 52, 456–467), liposome method, DEAE dextran method, etc.

A cell that is subjected to transformation could be any cell as long as the secretion signal sequence and expression regulating region contained in the vector functions within the cell, and preferable are, animal cells, for example, COS, CHO, or BAF3, etc.

In the second step ((ii)) of the method of the invention, a fusion protein of a secretable, functional protein having a binding affinity to the antigen and a protein encoded by a cDNA is expressed within cells. Specifically, cells are transformed using a vector containing DNA encoding the above-mentioned fusion protein, and are cultured under conditions suitable for cell growth. The culture is conducted according to commonly used methods. For example, DMEM, MEM, RPMI1640, and IMDM can be used as the culture medium and may be used together with serum-supplementing solutions such as fetal calf serum (FCS).

In order to express DNA within cells, a system that induces DNA expression can be used. For example, if expression regulating systems using tetracycline, or promoters/enhancers that are expressed in response to stimulations such as, cytokines, lipopolysaccharide (LPS), steroid hormones and such are used, it is possible to induce expression of DNA within cells by stimulating the cells. When DNA is expressed, a fusion protein containing gene products of the functional protein and cDNA is produced. When the cDNA encodes a membrane-bound protein, the secretion signal sequence is eliminated at the process when the fusion protein is synthesized on the rough endoplasmic reticulum (ER) and the fusion protein is expressed on the cell membrane. When DNA encoding a peptide linker is ligated between DNA encoding a functional protein and cDNA, a fusion protein comprising the peptide linker between the functional protein and cDNA is expressed.

The third step ((iii)) of the method of the invention involves selecting a cell binding to an antigen by contacting cells expressing a fusion protein on the cell membrane with the antigen. The antigen is preferably bound to a supporter. Examples of supporters are those for cell-culture, and preferably plates, such as plastic plates, multi-well plates, culture plates, or beads. Magnetic beads can be used as beads. The antigen can be bound to the supporter using commonly used methods. For example, the antigen can be bound to the supporter by adding the antigen to a plate in the presence of a suitable buffer, leaving overnight, and washing. The antigen may be bound to the supporter via an antibody that specifically binds to the antigen. For example, after an antibody specifically binding to an antigen is added to and fixed on the plate, the antigen can be added to bind it to the supporter. Alternatively, an antigen that is not bound to the supporter and a cell may be bound first, and then, the cell can be bound to the supporter using an antibody that specifically binds to the antigen immobilized upon the supporter. After binding the antigen unbound to the supporter and the cell, the antigen and cell can be crosslinked by crosslinking agents such as DMS (dimethylsulberimidate), $BS^3$ (bis (sulfosuccinimididyl) suberate, and DSS (disuccinimidyl suberate).

Cells unbound to the antigen are removed and cells bound to the antigen can be selected by incubating the plate under conditions where the cells can bind to the antigen on the plate and by washing the plate under suitable conditions after the cells are bound to the antigen. Flowcytometry (FACS) can also be used to select cells bound to the antigen. Cells selected by such methods are collected. By repeating these methods two to several times, the desired cells can be more selectively obtained.

Step four ((iv)) of the method of the invention involves isolating cDNA inserted within the vector from the selected cells.

First, the vector is extracted from the cells bound to the plate, in which the vector has been introduced, and cDNA contained in the vector is isolated. When a plasmid vector is used, the plasmid vector is extracted, introduced into *E. coli* amplified therein, and prepared to isolate cDNA. Next, the nucleotide sequence of the isolated gene is determined. Alternatively, a PCR primer is designed based on the nucleotide sequence on the vector, cDNA is amplified using this, and the nucleotide sequence is determined. When a retrovirus vector is used, cDNA is amplified by PCR in a similar manner, and the nucleotide sequence is determined.

The method of the present invention may include the step of analysis for determining whether the gene isolated above comprises a novel sequence or not. The novelty of the isolated DNA sequence may be analyzed by searching the homology of the sequence (the equivalence of the amino acid residues) using a DNA database, for example, GENBANK, EMBL, etc. The algorithm described in "Wilbur, W. J. and Lipman, D. J., Proc. Natl. Acad. Sci. USA (1983) 80, 726–730" may be followed to determine the homology of a protein.

The method of the present invention may also include the step of screening a cDNA library to obtain the full-length gene of the gene isolated above. Following commonly used methods, a cDNA library can be screened as follows. First, a fragment of the isolated gene is labeled, used as a probe, and hybridized to the cDNA library. The cDNA clone bound to the fragment of the isolated gene is then detected using the label.

The method of the present invention can also include the step of isolating the full-length gene of the gene isolated above. This can be done by screening the cDNA library as mentioned above, isolating cDNA clones detected by methods commonly known, and determining the nucleotide sequence thereof.

Furthermore, the present invention comprises a kit used for isolating a gene encoding the above-mentioned membrane-bound protein. The kit of the invention includes a vector having a restriction enzyme recognition site for inserting a cDNA downstream of the 3' side of a DNA encoding a secretable, functional protein having a binding affinity to an antigen. The kit of the invention preferably further includes, a supporter to which an antigen is bound and/or cells into which the vector is to be introduced. Additionally, wash solutions for panning, crosslinking agents for bridging cells with the antigen, a cDNA library, solutions for collecting DNA by dissolving the selected cells and such may also be contained.

BRIEF DESCRIPTION OF THE DRAWINGS

FIG. 6 shows a histogram obtained when the COS-7 cells into which various types of plasmid DNA have been introduced were analyzed by a flow cytometer using mouse anti-IL-6 receptor antibody MT-18.

BEST MODE FOR CARRYING OUT THE INVENTION

The cloning method of the invention can be specifically carried out as described below, but the present invention is by no means restricted thereto.

EXAMPLE 1

Construction of Expression Cloning Vector pTMT-SR345

Expression cloning vector pTMT-SR345 was constructed. SR345, encoded by the DNA contained in expression cloning vector pTMT-SR345, is the extracellular region portion of human IL-6 receptor, and consists of 345 amino acid residues from the N terminus. In the expression cloning vector pTMT-SR345, the protein encoded by cDNA inserted downstream of the DNA encoding SR345 is expressed as a fusion protein with SR345. The nucleotide sequence of SR345 is shown in SEQ ID NO: 2 together with the amino acid sequence.

First, in order to amplify the app. 1.1 kb fragment containing the cDNA encoding SR345 from the cDNA of IL-6 receptor (Yamasaki, K. et al, Science (1988) 241, 825–828), PCR primers IL6R1 (SEQ ID NO: 3) and IL6R2 (SEQ ID NO: 4) were designed. A PCR reaction mixture (100 ul) containing 10 mM Tris-HCl (pH8.3), 50 mM KCl, 0.1 mM dNTPs, 1.5 mM MgCl$_2$, 100 pmol each of the above-mentioned primers, 100 ng of template DNA (cDNA encoding IL-6 receptor), and 5 units of AmpliTaq Gold enzyme was subjected to denaturation at 94° C., incubated 30 cycles of 1 min at 94° C., 1 min at 55° C., and 1 min at 72° C., and finally, incubated for 10 min at 72° C. The amplified DNA fragment was collected and purified by 1% low melting point agarose gel electrophoresis, digested by EcoRI, and inserted into the EcoRI site of expression vector pCOS1. This was transfected into *E. coli*, and plasmids were prepared to obtain those in which the DNA fragment was inserted in the right direction. The expression vector pCOS1 was constructed from plasmid HEF-PMh-g γ1 (see WO92/19759) by deleting contained genes by EcoRI and SmaI digestion, and ligating with EcoRI-NotI-BamHI Adaptor (TaKaRa).

Figure 1:
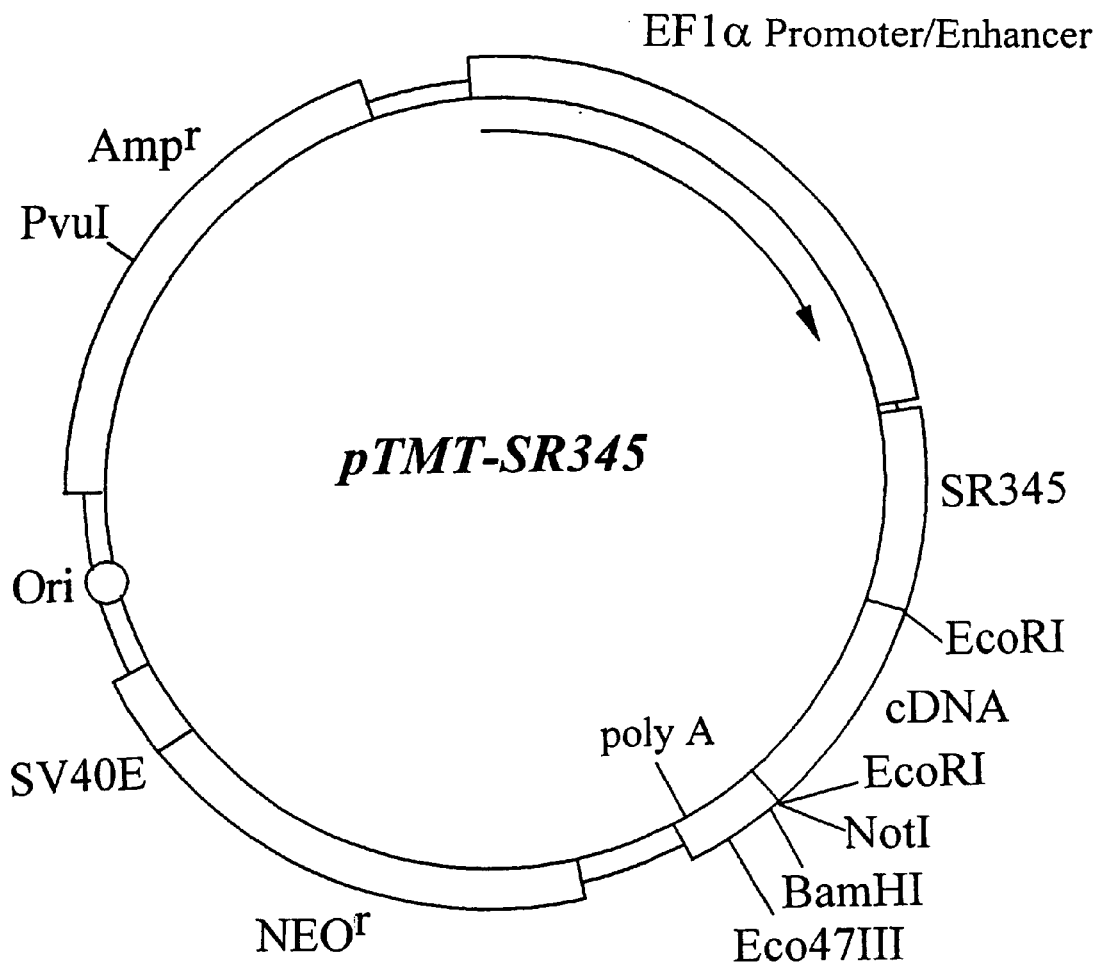
FIG. 1 schematically shows the structure of the expression cloning vector pTMT-SR345. "SR345" in the figure indicates human IL-6 receptor extracellular region, "NEO$^r$" the neomycin resistant gene, "EF1α" the promoter/enhancer region of peptide chain elongation factor Iα, "SV40E" the SV40 early promoter/enhancer, and "Amp$^r$" the ampicillin resistant gene.

Next, the EcoRI site in the upstream side of SR345 was removed by the following method. First, the plasmid was partially digested by EcoRI, and a linear molecule obtained by cleavage at one site was collected. This was blunt-ended by DNA polymerase I (Klenow fragment), self-ligated, and transfected into *E. coli* to obtain expression cloning vector pTMT-SR345. The structure of the expression cloning vector pTMT-SR345 is shown in FIG. 1.

EXAMPLE 2

Construction of Expression Vector pTMT-scFv

Expression vector pTMT-scFv was constructed. The single-chain antibody (scFv) encoded by the DNA contained in the expression vector pTMT-scFv was designed using the variable region of the humanized monoclonal antibody PM-1, which recognizes human IL-6 receptor, and a linker region. In the expression vector pTMT-scFv, the protein encoded by the cDNA inserted downstream of the DNA encoding scFv, is expressed as a fusion protein with scFv. The nucleotide sequence of scFv gene is shown in SEQ ID NO: 5 together with the amino acid sequence.

1) Amplification of the DNA Fragment Encoding Antibody V Region

The genes of humanized PM1 antibody H chain and L chain V region (Sato, K et al, Cancer Res. (1993) 53, 851–856) were amplified by PCR. Backward primer TMT1 (SEQ ID NO: 6) for H chain V region was designed in such a manner that it should hybridize to DNA encoding the N terminus of H chain V region and comprise a SalI restriction enzyme recognition site. Forward primer LINK1 (SEQ ID NO: 7) for H chain V region was designed in such a manner that it should hybridize to DNA encoding the C terminus of H chain V region and comprise 5' end sequence of a linker region. Also, backward primer LINK3 (SEQ ID NO: 8) for L chain V region was designed in such a manner that it should hybridize to DNA encoding the N terminus of L chain V region and comprise 3' end sequence of a linker region. Forward primer SCP-C (SEQ ID NO: 9) for L chain V region was designed in such a manner that it should hybridize to the nucleotide sequence encoding the amino acid sequence forming L chain constant region elbow site, and also comprise HindIII restriction enzyme recognition site, nucleotide sequence encoding FLAG peptide (SEQ ID NO: 10), and two repetitive translation stop codons.

A PCR reaction mixture (100 ul) containing 10 mM Tris-HCl (pH8.3), 50 mM KCl, 0.1 mM dNTPs, 1.5 mM MgCl$_2$, 100 pmol each of the above-mentioned primers, 100 ng of template DNA, and 5 units of AmpliTaq Gold enzyme was subjected to denaturation at 94° C. for 9 min, incubated 30 cycles of 30 sec at 94° C. and 1 min at 60° C., and finally, incubated for 5 min at 60° C. The PCR product was purified using a 1.5% low melting point agarose gel.

2) Amplification of the DNA Fragment Encoding a Linker Region

The DNA fragment encoding a linker region comprising the amino acid sequence of (Gly$_4$Ser)$_3$ was amplified by the PCR method using humanized single-chain antibody;

expression vector pSCFVT7-hM21 (see WO95/14041). Backward primer LINK2 (SEQ ID NO: 11) was designed in such a manner that it should hybridize to the 5' end of the linker region, and also comprise the 3' end DNA sequence of H chain V region. Forward primer LINK4 (SEQ ID NO: 12) was designed in such a manner that it should hybridize to 3' end of the linker region, and also comprise the DNA sequence of 5' end of L chain V region. PCR was conducted using 100 ng of template DNA(pSCFVT7-hM21) under the conditions above-mentioned, and the PCR product was purified using a 1.5% low melting point agarose gel.

3) Construction of Humanized PM1 Antibody Single-chain Fv

The DNA fragment encoding H chain and L chain V regions prepared above, and the DNA fragment encoding the linker region were assembled by the PCR method, and backward primer TMT1 and forward primer TMT2 (SEQ ID NO: 13) were added to amplify the full-length DNA fragment encoding scFv of humanized PM1. The forward primer TMT2 was designed in such a manner that it should hybridize to the DNA sequence encoding HindIII restriction enzyme recognition site and FLAG peptide, and also comprise two repetitive translation stop codons, and the EcoRI restriction enzyme recognition site. The primary PCR was conducted as follows: 98 ul of a PCR reaction mixture containing 10 mM Tris-HCl (pH8.3), 50 mM KCl, 0.1 mM dNTPs, 1.5 mM $MgCl_2$, app.100 ng each of the above PCR products, and 5 units of AmpliTaq Gold enzyme was subjected to denaturation first at 94° C., and then 2 cycles of 2 min at 94° C., 2 min at 55° C., and 2 min at 72° C. were done to ligate each DNA fragment. The secondary PCR was done in the following manner: 100 pmol of each primer was added to the above PCR reaction solution, 30 cycles of 30 sec at 94° C. and 1 min at 60° C. were done, and finally, the mixture was incubated for 5 min at 60° C.

Figure 2:
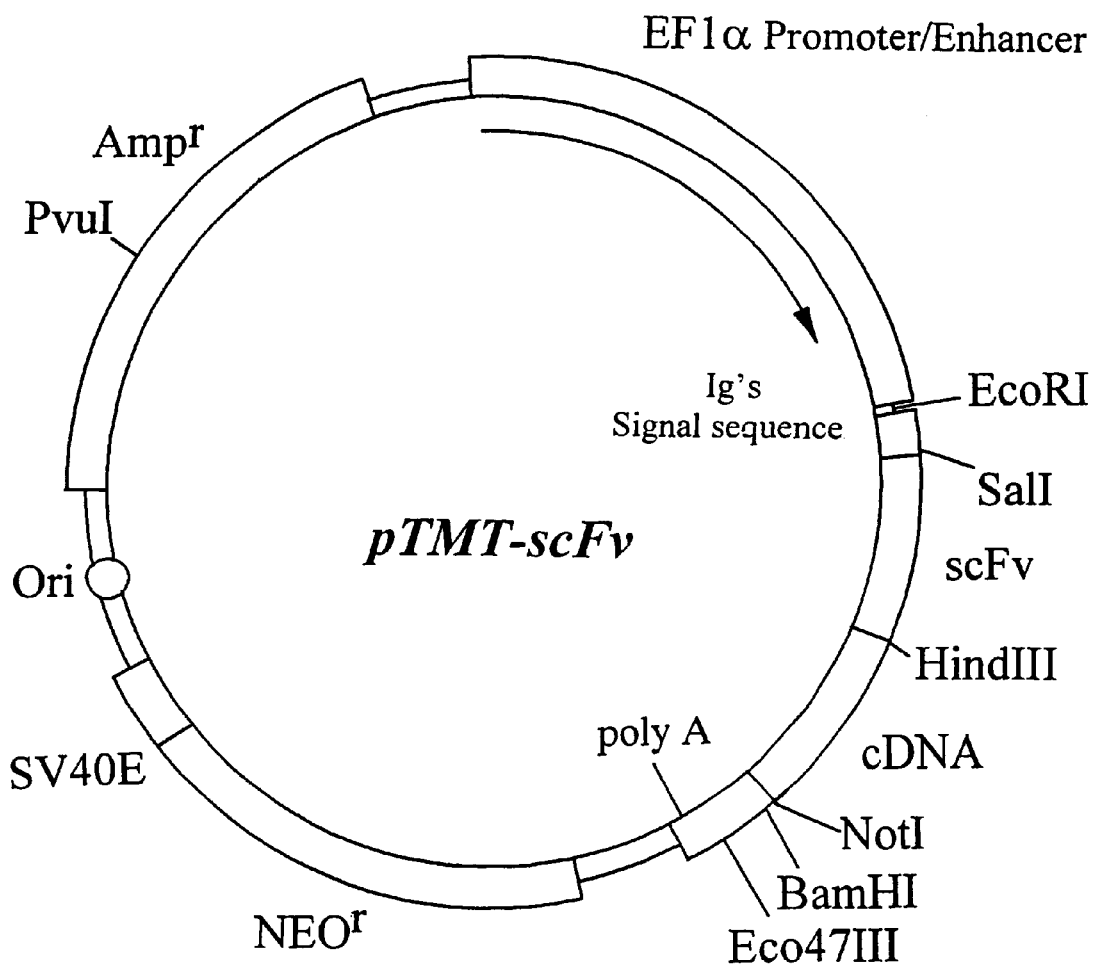
FIG. 2 schematically shows the structure of the expression vector pTMT-scFv. "scFv" in the figure indicates single-chain antibody, and "Ig's" the antibody secretion signal peptide. The other symbols are the same as FIG. 1.

After the PCR product was purified using a 1.5% low melting point agarose gel, it was digested by SalI and NotI, and inserted into expression vector PSFLAG comprising human EF1α promoter and the leader sequence of the antibody (SEQ ID NO:14). After DNA sequencing, plasmid pTMT-scFv, containing a DNA fragment comprising the correct DNA sequence, was obtained. The structure of the expression vector pTMT-scFv is schematically shown in FIG. 2. The construction of pSFLAG was done as mentioned below. Two overlapping oligonucleotides S-FLAG1 (SEQ ID NO: 15) and S-FLAG2 (SEQ ID NO: 16) in the sense and antisense directions, respectively, were designed and synthesized so as to encode EcoRI restriction enzyme recognition site, the leader sequence of the antibody (SEQ ID NO: 14), FLAG peptide (SEQ ID NO: 10), and KpnI, NotI, and BamHI restriction enzyme recognition sites. A reaction mixture containing 100 pmol each of the synthesized oligonucleotides was incubated for 5 min at 96° C., and the temperature was lowered to 65° C. over 20 min, and incubated for 5 min at 65° C. Then, the temperature was lowered to 42° C. over 20 min, the mixture was incubated for a further 5 min. and the two oligonucleotides were annealed by lowering the temperature to room temperature over 20 min. This DNA fragment was inserted into pCOS1 digested by EcoRI and BamHI.

EXAMPLE 3

Construction of SR345-gp130 and scFV-gp130 Fusion Protein Expression Systems (A) SR345-gp130

The cytokine signal transduction molecule gp130 is a type I membrane-bound protein (Taga, T. et al., Cell (1989) 58, 573–581, Saito, M., et al., J. Immunol. (1992) 148, 4066–4071). Aportion of mouse gp130 cDNA was ligated downstream of a cDNA encoding soluble-type IL-6 receptor (SR345) of the expression vector pTMT-SR345, to express a fusion protein comprising SR345 and a partial sequence of mouse gp130, in COS cells. Two types of fusion proteins were constructed according to their differences in the gp130 partial regions. One of them is a membrane-bound fusion protein (SR345-mgpTMIC) in which the transmembrane region of gp130 and the subsequent intracellular region are ligated, and the other is a secretory fusion protein (SR345-mgpIC) in which only the intracellular region of gp130 is ligated. SEQ ID NO: 17 shows the amino acid sequence and the nucleotide sequence of full-length mouse gp130.

1) Creation of the Membrane-bound Fusion Protein SR345-mgpTMIC Expression Vector The full-length mouse gp130 cDNA was digested with EcoRI to obtain an EcoRI fragment of app. 1.1 kb. This EcoRI fragment encodes amino acids from the position $603^{rd}$ to the position $917^{th}$ (C terminus) of mouse gp130, and contains a portion (15 amino acids) of the extracellular region of mouse gp130 and the whole of the subsequent transmembrane region and the intracellular region. This EcoRI fragment was inserted into the EcoRI site of pTMT-SR345 expression vector to create the membrane-bound fusion protein SR345-mgpTMIC expression vector.

2) Creation of Secretory Fusion Protein SR345-mgpIC Expression Vector

To obtain a cDNA fragment encoding the intracellular region of mouse gp130, the PCR primers mgp2 (SEQ ID NO: 20; including DNA encoding the $646^{th}$ amino acid to the $651^{th}$ amino acid of the amino acid sequence of SEQ ID NO: 17), to which the HindIII and EcoRI sites had been added, and mgp3 (SEQ ID NO: 19; including DNA encoding the $912^{th}$ amino acid to the $917^{th}$ amino acid (C terminus) of the amino acid sequence of SEQ ID NO: 17) were synthesized, and using these primers, an app. 1 kb cDNA fragment of mouse gp130 was obtained. This app. 1 kb cDNA fragment encodes the $646^{th}$ amino acid to the $917^{th}$ amino acid in the amino acid sequence of SEQ ID NO: 17, and this corresponds to the intracellular region in which six amino acids from the N terminus are lacking. The cDNA fragment thus obtained, was digested with EcoRI, and inserted into EcoRI site of pTMT-SR345 expression vector to prepare the secretory fusion protein SR345-mgpIC expression vector.

(B) scFv-gp130

In the expression vector pTMT-scFv, a portion of mouse gp130 cDNA was ligated downstream of scFv cDNA to express a fusion protein comprising scFv and a partial region of mouse gp130 in COS cells. Two types of fusion proteins were constructed according to their differences in the ligated gp130 partial regions. One of them is a membrane-bound fusion protein (scFv-mgpTMIC) in which the transmembrane region of gp130 and the subsequent intracellular region are ligated, and the other is secretory fusion protein (scFv-mgpIC) in which only the intracellular region of gp130 is ligated.

1) Creation of Membrane-bound Fusion Protein scFv-mgpTMIC Expression Vector

To obtain a cDNA fragment encoding the whole intracellular region and transmembrane region of mouse gp130, the PCR primers mgp1 (SEQ ID NO: 18; including DNA encoding the $603^{rd}$ amino acid to the $608^{th}$ amino acid in the amino acid sequence of SEQ ID NO: 17), to which the HindIII site had been added, and mgp3 (SEQ ID NO: 19;

including DNA encoding the 912$^{th}$ amino acid to the 917$^{th}$ amino acid (C terminus) of the amino acid sequence of SEQ ID NO: 17), to which the NotI site had been added, and using these primers, an app. 1.1 kb cDNA fragment of mouse gp130 was obtained. This app. 1.1 kb cDNA fragment encodes the 603$^{rd}$ amino acid to the 917$^{th}$ amino acid (C terminus) in the amino acid sequence of SEQ ID NO: 17, and this comprises a part of the extracellular region of mouse gp130 (15 amino acids) and the whole of the subsequent transmembrane region and the intracellular region. The cDNA fragment thus obtained was digested with HindIII and NotI, and inserted into the HindIII-NotI sites of pTMT-scFv expression vector to prepare the membrane-bound fusion protein scFv-mgpTMIC expression vector.

2) Creation of the Secretory Fusion Protein scFv-mgpIC Expression Vector

To obtain a cDNA fragment encoding the intracellular region of mouse gp130, the PCR primers mgp2 (SEQ ID NO: 20; including DNA encoding the 646$^{th}$ amino acid to the 651$^{st}$ amino acid in the amino acid sequence of SEQ ID NO: 17), to which the HindIII-EcoRI sites had been added, and mgp3 (SEQ ID NO: 19; including DNA encoding the 912$^{th}$ amino acid to the 917$^{th}$ amino acid (C terminus) of the amino acid sequence of SEQ ID NO: 17), to which the NotI site had been added, were synthesized, and, by PCR using these primers, an app. 1 kb cDNA fragment of mouse gp130 was obtained.

This app. 1 kb cDNA fragment encodes the 646$^{th}$ amino acid to the 917$^{th}$ amino acid (C terminus) in the amino acid sequence of SEQ ID NO: 17, and this corresponds to the intracellular region in which six amino acids from the N terminus are lacking. The cDNA fragment thus obtained was digested with HindIII and NotI, and inserted into HindIII-NotI sites of the expression vector pTMT-scFv to prepare the secretory fusion protein scFv-mgpIc expression vector.

EXAMPLE 4

Expression by COS Cells

Each type of the above-mentioned expression vectors was transfected into COS cells, the fusion protein was transiently expressed, and it was verified that cells expressing the fusion protein on the cell membrane were selectively condensed by panning. COS cells transfected with the expression vector not containing genes were used as the negative control. The positive control were COS cells that were transfected with the expression vector P3.19, which was prepared by introducing DNA encoding the HM1.24 antigen protein (WO 98/14580) into the vector pCOS1, and that were panned with the corresponding antibody.

1) Transfection into COS Cells

The plasmid DNA was transfected into COS-7 cells using Lipofect AMINE PLUS™ Reagent (GIBCO-BRL). Namely, COS-7 cells seeded in 1×10$^5$ cells/well (6-well plate) on the day prior to the transfection were cultured overnight, and washed with serum-free DMEM culture medium (GIBCO-BRL), and then 0.8 ml of the same culture medium was added thereto. Separately, after 1 μg of plasmid DNA and 6 μl of PLUS Reagent were added to 0.1 ml serum-free DMEM culture medium, the mixture was incubated for 15 min at room temperature, mixed with 0.1 ml of Lipo-fectAMINE solution (4 μl of LipofectAMINE/0.1 ml of serum-free DMEM:culture medium) and incubated for further 15 min at room temperature. Next, this mixture was added to the above-mentioned COS-7 cells and incubated for 3 hours at 37° C. DMEM culture medium (1 ml) containing 20% fetal calf serum (GIBCO-BRL) was added thereto (final concentration 10% serum). Following an overnight culture, the culture medium was changed to 3 ml of DMEM culture medium containing 10% fetal calf serum, and incubated for 3 days under the conditions of 37° C. and 5% $CO_2$.

2) Preparation of the Panning-dish

When using the expression vector pTMT-SR345, a dish coated with the mouse anti-human IL-6 receptor antibody MT18 (see unexamined published Japanese patent application No. Hei 2–288898) was prepared according to the method of Seed, B. et al., Proc. Natl. Acad. Sci. USA. (1987) 84, 3365–3369. Namely, mouse anti-IL-6 receptor antibody was added to 50 mM Tris-HCl (pH9.5) to 10 μg/ml. The antibody solution thus prepared (3 ml) was incubated at room temperature for two hours in a 60 mm-diameter cell culture dish. After washing the culture dish three times with a 0.15M NaCl solution, PBS containing 5% fetal calf serum, 1 mM EDTA, and 0.02% $NaN_3$ was added, and then after blocking, panning was done as mentioned below.

When using pTMT-scFv, two types of panning dishes were prepared. One was coated with soluble-type IL-6 receptor (SR344) (Yasukawa, K. et al., J. Biochem. (1990) 108, 673–676), and the other was coated with the above-mentioned mouse anti-IL-6 receptor antibody. The concentration of SR344 was adjusted to 2 μg/ml with 50 mM Tris-HCl (pH9.5), and a panning dish was prepared as mentioned above. When the negative control pCOS-1 was used, a dish coated with the above-mentioned mouse anti-IL-6 receptor antibody was utilized. When the positive control HM1.24 antigen protein expression vector P3.19 was used, a dish coated with the antibody against HM1.24 antigen was utilized.

3) Panning pCOS-1- or, pTMT-SR345-transfected: COS-7 cells were detached from the plate by 1 MM EDTA containing PBS, washed once with PBS containing 5% fetal calf serum, suspended in 2 ml of PBS containing 5% fetal calf serum and 0.02% $NaN_3$, and added to the panning plate coated with mouse anti-IL-6 receptor antibody.

pTMT-scFv-transfected COS-7 cells were panned by three different methods. In one method, after detached as mentioned above and washed once with PBS containing 5% fetal calf serum, COS-7 cells were suspended in 500 μl of PBS containing 2μg/ml SR344, 5% fetal calf serum, and 0.02% $NaN_3$, and incubated on ice for 1 hr. After washing three times with ice-cold PBS, the cells were resuspended in PBS containing 0.2 mM crosslinker bis(sulfosuccinimidyl) suberate ($BS^3$; PIERCE) and 50 mM Hepes (pH8.0), and further incubated on ice for 30 min. Then, 1 M Tris-HCl (pH8.0) was added to 50 mM, and incubated further on ice for 10 min to remove the excess amount of the crosslinker. After washing cells with PBS, they were added to a panning plate coated with mouse anti-IL-6 receptor antibody. In the second method, COS-7 cells preincubated with SR344 were added to the panning plate coated with mouse anti-IL-6 receptor antibody without crosslinker treatment. In the third method, COS-7 cells were added to a plate directly coated with SR344. The time of incubation on ice, Tris-HCl treatment, and washing were similar in all the three methods.

Figure 3:
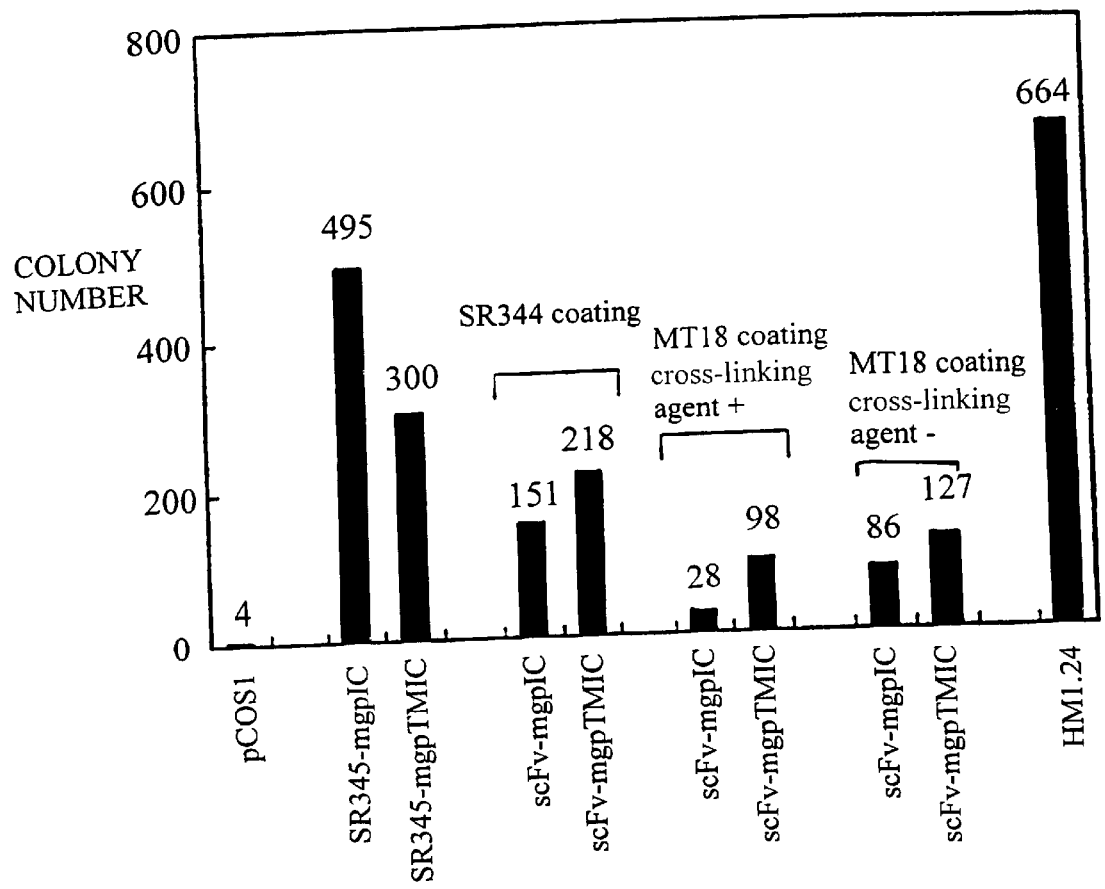
FIG. 3 shows the colony number recovered by panning using COS-7 cells into which various types of plasmid DNA have been introduced.

COS-7 cells transfected with the HM1.24 antigen protein expression vector P3.19 were added to a panning plate coated with the antibody against HM1.24 antigen (WO 98/14580). After incubating the above-mentioned various types of COS-7 cells on the various panning plates for 2 hr at room temperature, the plates were gently washed three times with PBS containing 5% fetal calf serum and 0.02% $NaN_3$, and plasmid DNAs were collected from cells bound to the panning dishes using 0.6% SDS and 10 mM EDTA-containing solution. The condensation effect due to panning was evaluated by transfection of a $\frac{1}{5}^{th}$ of the recovered plasmid DNA into E. coli DH5a using electroporation, and by the number of ampicillin-resistant colonies that had appeared. The results are shown in FIG. 3.

When the expression vector pTMT-SR345 was used, SR345-mgpIC resulted in more colonies than SR345-mgpTMIC, and therefore, no specificity against the membrane-bound protein was seen. On the other hand, when using expression vector pTMT-scFv, in all panning methods, scFv-mgpTMIC resulted in more colonies than scFv-mgpIC, and therefore, cells expressing membrane-bound protein were specifically condensed. The selectivity was more evident especially when a crosslinking agent was used.

Thus, the above-mentioned results show that cDNA encoding a membrane-bound protein was more selectively and efficiently obtained by expressing the functional protein (single-chain antibody) as a fusion protein on the cell surface than by expressing just an epitope recognized by the antibody as the fusion protein.

Generally, several repetitive pannings enhance the clone-selectivity, but, as shown by the present example, in the present invention, in which a functional protein is expressed on the cell membrane, an outstanding selectivity was observed in the first panning. Therefore, cloning of a gene encoding a membrane-bound protein can be extremely efficiently and selectively accomplished by panning further several times.

EXAMPLE 5

Construction of the Fusion Protein Expression System using Humanized Bivalent Single-chain Fv 1. Construction of the Humanized PM1 Antibody Bivalent Single-chain Fv Expression Vector A bivalent single-chain Fv expression vector was constructed based on humanized PM1 antibody Fv. The humanized PM1 antibody single-chain Fv (hPM1-BvGS3) having a bivalent variable region was designed so that two molecules of the humanized PM1 antibody single-chain Fv2 described in Example 2 were ligated via a peptide linker comprising (Gly$_4$Ser)$_3$ (SEQ ID NO: 1). The amino acid sequence and nucleotide sequence of hPM1-BvGS3 are shown in SEQ ID NO: 21.

The construction of expression vector pTMT-BvGS3 was done as follows. A gene encoding a humanized PMI antibody single-chain Fv having, in its C terminus, a linker comprising (Gly$_4$Ser)$_3$ was amplified by the PCR method. TMT-1 (SEQ ID NO: 6) was used as the backward primer. Also, the forward primer BvGS3 (SEQ ID NO: 22) was designed in such a manner that it should hybridize to DNA encoding the C terminus of L chain V region and also comprise the nucleotide sequence encoding the linker and restriction enzyme SalI recognition site. PCR was conducted using 100 ng of pTMT-scFv as the template DNA under the same conditions as mentioned above, and the PCR product was purified using 1.5% low melting point agarose gel.

Figure 4:
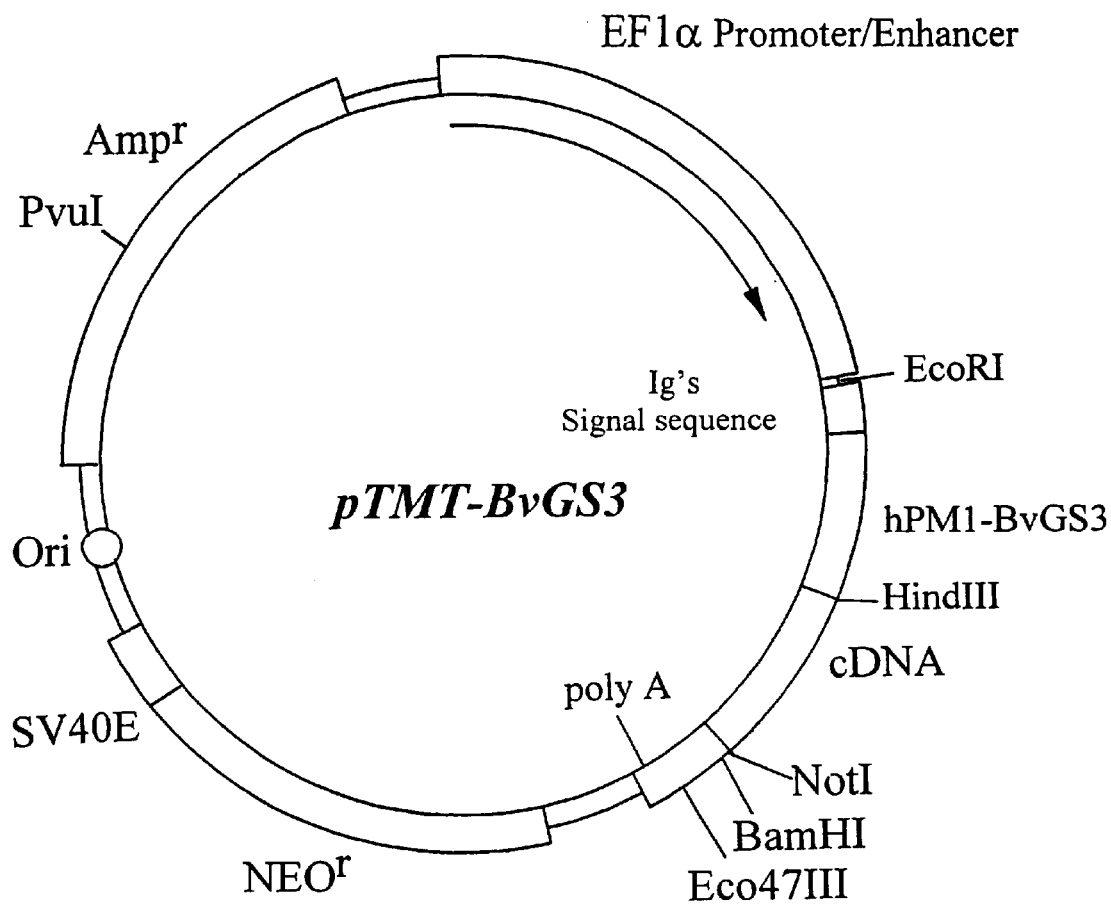
FIG. 4 schematically shows the structure of the expression vector pTMT-BvGS3. "hPM1-BvGS3" in the figure indicates bivalent single-chain antibody. The other symbols are the same as FIG. 1 and FIG. 2.

The purified PCR product was digested with restriction enzyme SalI, and inserted into the cloning vector pBluescriptII (Stratagene). After DNA sequencing, the plasmid containing the DNA fragment comprising the correct DNA sequence was digested with restriction enzyme SalI, to obtain a gene encoding humanized PM1 antibody single-chain Fv having, in its C terminus, a linker comprising (Gly$_4$Ser) 3. Next, by inserting the DNA fragment obtained as mentioned above into pTMT-scFv, hPM1-BvGS3 expression vector TMT-BvGS3 was obtained. The structure of the hPM1-BvGS3 expression vector pTMT-BvGS3 is schematically shown in FIG. 4.

2. Construction of Fusion Protein hPM1-BvGS3-gp130 Expression Vector

In the expression vector pTMT-BvGS3, a portion of the mouse gp130 cDNA was ligated downstream of the cDNA encoding hPM1-BvGS3 to construct a fusion protein expression system comprising hPM1-BvGS3 and a partial region of mouse gp130. Two types of fusion proteins were constructed according to their differences in the gp130 partial regions that are ligated. One of them is a membrane-bound fusion protein (BvGS3-mgpTMIC) in which the transmembrane region of gp130 and the subsequent intracellular region are ligated, and the other is secretory fusion protein (BvGS3-mgpIC) in which only the intracellular region of gp130 is ligated. BvGS3-mgpTMIC and BvGS3-mgpIC were those prepared in Example 3 (B)-1) and 2), respectively, and by inserting these into the HindIII-NotI sites of pTMT-BvGS3, membrane-bound fusion protein expression vector pTMT-BvGS3-mgpTMIC and secretory fusion protein expressing vector pTMT-BvGS3-mgpIC were constructed.

EXAMPLE 6

Analysis of Expression by a Flow Cytometer

Each type of the expression vectors constructed above, pTMT-BvGS3, pTMT-BvGS3-mgpIC, and pTMT-BvGS3-mgpTMIC, was transfected into COS-7 cells, the fusion protein was transiently expressed, and the expression on the cell membrane was analyzed with a flow cytometer (FACScan, Beckton Dickinson). The expression analysis was conducted by two types of methods. One involved detection by a rabbit polyclonal antibody against humanized PM-1 antibody, and the other involved detection by mouse anti-IL-6 receptor antibody MT-18 in the presence of soluble IL-6 receptor antibody. As a result, it was confirmed that the membrane-bound fusion protein BvGS3-mgpTMIC was strongly expressed on the cell membrane in a form that could recognize soluble IL-6 receptor. Cells transfected with expression vector pCOS-1 only were used as the negative control.

1) Transfection Into COS-7 Cells

The plasmid DNA was transfected into COS-7 cells using the transfection kit FuGENE™6 (Boehringer-Mannheim).

Namely, COS-7 cells seeded in 5×10$^4$ cells/well (6-well plate) on the day prior to the transfection were cultured overnight under the conditions of 37° C. and 5% CO$_2$ in 2 ml of DMEM culture medium (GIBCO-BRL) containing 10% fetal calf serum. On the day of transfection, 6 µl of FuGENE™6 was added to 0.1 ml of serum-free DMEM culture medium and, after incubating for 5 min at room temperature, was mixed with 2 µg of plasmid DNA, and incubated for further 15 min at room temperature. Next, this mixture was added to the above-mentioned COS-7 cells and incubated for three days under the conditions of 37° C. and 5% CO$_2$.

2) Staining of COS-7 Cells

The above-mentioned COS-7 cells were detached with PBS containing 1 mM EDTA, washed with PBS containing 5% fetal calf serum, suspended in 50 µl of FACS buffer (PBS containing 2% fetal calf serum and 0.05% NaN$_2$), and stained by the following two types of methods.

A) Staining with a Rabbit Polyclonal Antibody Against Humanized PM-1 Antibody

A rabbit polyclonal antibody against humanized PM-1 antibody (2 µg/reaction) was added to the above-mentioned COS-7 cells, incubated for 30 min on ice, washed twice with 1 ml FACS buffer, and resuspended in 50 μl of FACS buffer. Next, 2 μl/reaction of FITC (fluorescein isothiocyanate)-labeled goat anti-rabbit IgG (AMERICAN QUAREX) and, for separately staining dead cells, 2.5 μg/reaction of PI (propidium iodide) were added and incubated for30 min on ice in the dark. After the incubation, the cells were washed twice with 1 ml of FACS buffer, and resuspended in 0.5 ml of FACS buffer to analyze with a flow cytometer.

B) Staining with Mouse Anti-IL-6 Receptor Antibody MT-18

Soluble-type IL-6 receptor (3 μg/reaction) was added to the above-mentioned COS-7 cells and incubated for 4 hr on ice, washed twice with 1 ml FACS buffer, and resuspended in 50 μl of FACS buffer. Next, 2 μg/reaction of mouse anti-IL-6 receptor antibody MT-18 was added and incubated for 30 min on ice. After the incubation, the cells were washed twice with 1 ml of FACS buffer and resuspended in 50 μl of FACS buffer. Next, 2 μl/reaction of FITC-labeled goat anti-mouse IgG2b (Dainippon Seiyaku) and, for separately staining dead cells, 2.5 μg/reaction PI (propidium iodide) were added and incubated for 30 min on ice in the dark. After the incubation, the cells were washed twice with 1 ml of FACS buffer, and resuspended in 0.5 ml of FACS buffer to analyze with a flow cytometer.

3) Analysis of Expression with a Flow Cytometer

Analysis by PI and FSC (Forward Scatter) revealed that a population of cells stained with PI (dead cells) was present. Dead cells disturb the analysis as they are non-specifically stained with FITC. Hence, the cell-population that was not stained with PI (living-cells) was gated, and analysis was carried out for this population only.

Figure 5:
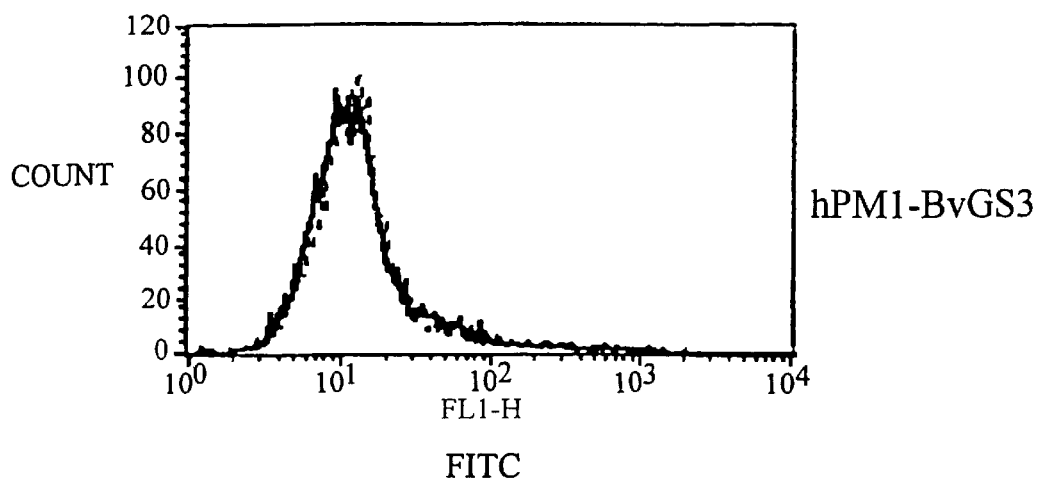
FIG. 5 shows a histogram obtained when the COS-7 cells into which various types of plasmid DNA have been introduced were analyzed by a flow cytometer using a rabbit polyclonal antibody against humanized PM-1 antibody.
Figure 5:
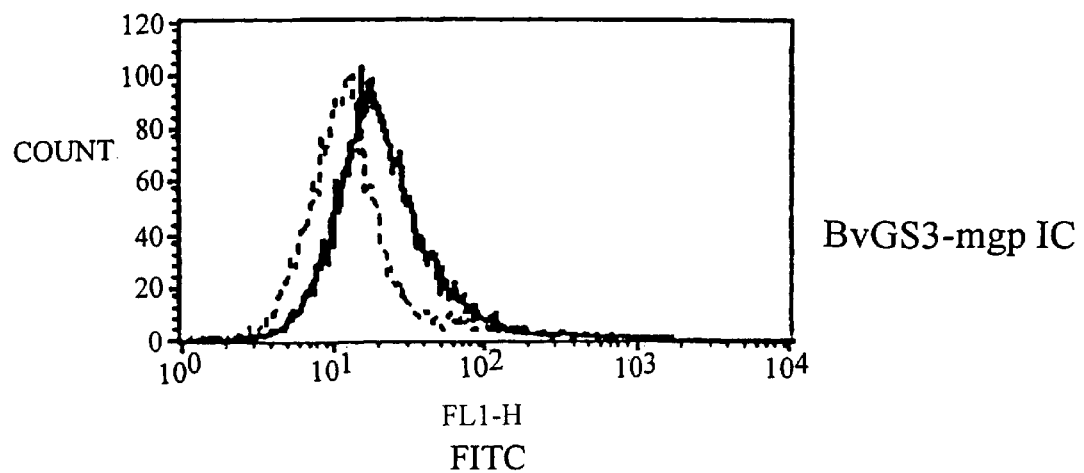
Figure 5:
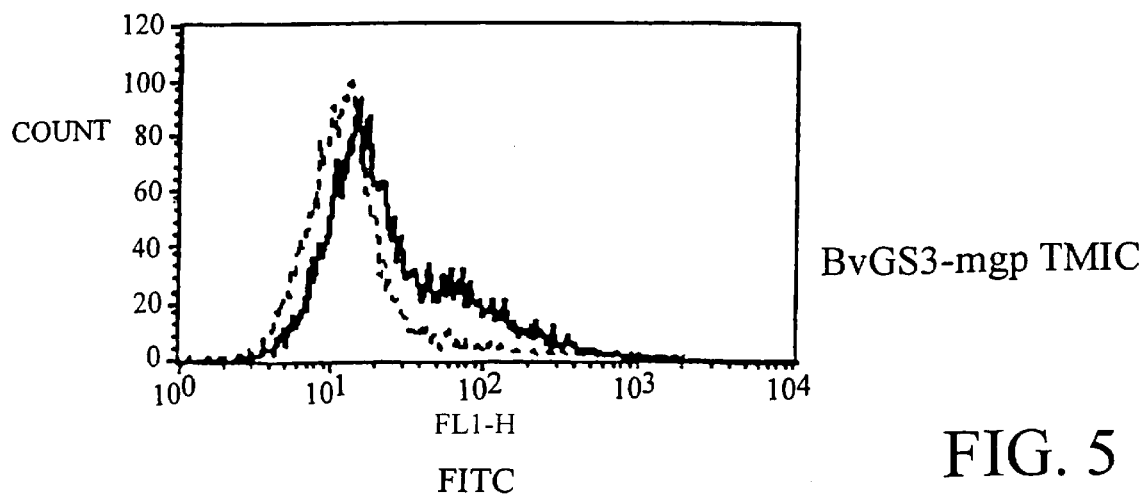

As a result of staining with the rabbit polyclonal antibody against humanized PM-1 antibody, no expression of secretory protein hPM1-BvGS3 was seen on the cell membrane, however, the expression of membrane-bound fusion protein BvGS3-mgpTMIC showed the strongest expression. From this fact, it is presumed that BvGS3-mgpTMIC, which has a transmembrane region, is not secreted and is trapped in the cell membrane. However, on the other hand, the expression of BvGS3-mgpIC was detected on the cell membrane, despite the fact that it is a secretory fusion protein. This is presumed to be due to the fact that the characteristics of BvGS3-mgpIC are different from that of BvGS3 in the molecular size and structure, hydrophobic region contained in the mgpIC connected downstream thereof, etc. Namely, it is presumed that, due to its difference in characteristics, BvGS3-mgpIC does not pass through the cell membrane as swiftly as BvGS3 does, and it takes more time to pass through. As a result, the amount localized on the cell membrane increases, and all whose epitopes are extruding extracellulary are detected by a rabbit polyclonal antibody against humanized PM-1. The results are shown in FIG. 5.

Figure 6:
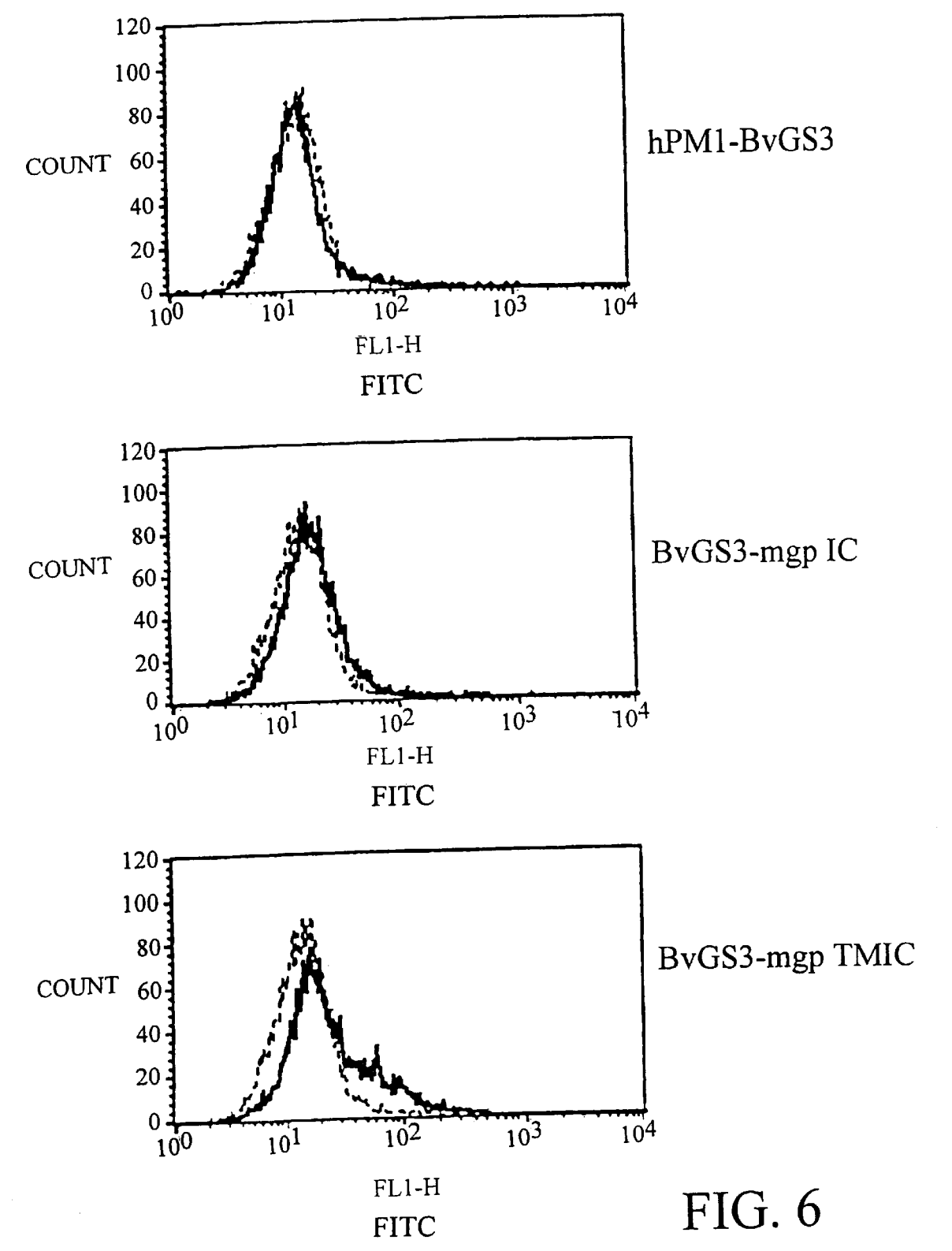

On the other hand, in the case of staining with mouse anti IL-6 receptor antibody MT-18, similar to the results of staining by rabbit polyclonal antibody against humanized PM-1 antibody, though expression was not detected for secretory protein hPM1-BvGS3, the expression of membrane-bound fusion protein BvGS3-mgpTMIC was the strongest. However, for the secretory fusion protein BvGS3-mgpIC, the results were different from those obtained by rabbit polyclonal antibody against humanized PM-1 antibody, and any expression was hardly detected on the cell membrane. This indicates that, while the membrane-bound fusion protein BvGS3-mgpTMIC is expressed on the cell membrane forming a functional conformation that could recognize soluble-type IL-6 receptor, most of the secretory fusion protein BvGS3-mgpIC, though localized on the cell membrane, does not have a functional conformation that could recognize soluble-type IL-6 receptor. The results are shown in FIG. 6.

Thus, the results obtained by the flow cytometer suggests that when a mere epitope recognized by an antibody is expressed as a fusion protein, even secretory fusion proteins will be selected as false-positive if they are localized on the cell membrane. On the other hand, when the functional protein of the invention (for example, single-chain antibody) is expressed on cell surface as a fusion protein, the possibility of cloning cDNA encoding a membrane-bound protein more selectively and efficiently has been revealed.

EXAMPLE 7

1. Designing of Humanized PM1 Antibody Single-chain Fv

In order to improve the cloning efficiency, three other types of single-chain Fv and their bivalent single-chain Fv were designed. Since the elbow region (SEQ ID NO: 5, amino acid sequence from the $242^{nd}$ to $256^{th}$ positions), added at the time of constructing above-mentioned humanized PM1 antibody single-chain Fv, contained amino acids residues with high hydrophobicity, the following three types of humanized PM1 antibody single-chain Fv were designed for more stable extracellular expression.

Namely, in order to remove the hydrophobic region in the C terminus, single-chain Fv depleted of the elbow region was designed and designated as shPM1(ΔEL) (SEQ ID NO: 23). Also, since it was perceived that the stability and expression efficiency would increase by adding a certain secretory protein-derived domain to the C terminus of single-chain Fv, the amino acid sequence encoded by human κ chain constant region or human membrane-type μ chain constant region exon 4 (Dorai, H and Gillies S. D. Nucleic Acid Res., 17, 6412, 1989) was added to the C terminus of single-chain Fv (SEQ ID NO: 23). Although the $107^{th}$ amino acid residue of human κ chain constant region is originally cysteine, one replaced with serine residue (SEQ ID NO: 24) was used this time. Also, the sequence from which transmembrane region and intracellular region had been deleted (SEQ ID NO: 25) was used as the amino acid sequence encoded by human membrane-type μ chain constant region exon 4. Those in which respective sequences mentioned above were added to the C terminus of single-chain Fv were termed shPM1-Kappa (SEQ ID NO: 26) and shPM1-MCH4 (SEQ ID NO: 27).

2. Construction of the shPM1(ΔEL) Expression Vector

The gene encoding shPM1(ΔEL) was amplified by PCR method. The backward primer EF-1 (SEQ ID NO: 28) and the forward primer SCP-C2 (SEQ ID NO: 29) were used. PCR was conducted using 100 ng of pTMT-scFv as template DNA under the conditions mentioned above, and the PCR product was purified using 1.5% low melting point agarose gel. The forward primer SCP-C2 was hybridized to DNA encoding the C-terminus of L chain V region, and, nucleotides encoding restriction enzyme HindIII-NotI recognition sites and FLAG peptide (SEQ ID NO: 10) were added thereto.

After the purified PCR product was digested with EcoRI and NotI, the digested product was inserted into PSFLAG vector to obtain the shPM1(ΔEL) expression vector pTMT-shPM1F. Moreover, pTMT-shPM1F-BvGS3, the expression vector for shPM1(ΔEL)-BvGS3 (SEQ ID NO: 30), single-chain Fv which had a bivalent variable region and whose elbow region had been deleted, was obtained by a similar method to that in Example 5.

3. Construction of the shPM1Kappa Expression Vector

The gene encoding the fusion protein of humanized PM1 antibody single-chain Fv (SEQ ID NO: 23) and human κ chain constant region (SEQ ID NO: 24) was constructed by PCR assembling. Namely, after the genes encoding humanized PM1 antibody single-chain Fv and human κ chain constant region were separately amplified by PCR, they were assembled by their complementarity and the full-length gene was amplified by the external primer.

First, the gene encoding human κ chain constant region was amplified by PCR. The backward primer Kappa1 (SEQ ID NO: 31) was designed in such a manner that it should hybridize to the nucleotide sequence encoding the elbow region of human κ chain constant region and the $12^{th}$ position Pro to the $21^{st}$ position Gly of the following amino acid sequence (SEQ ID NO: 24). The forward primer Kappa2 (SEQ ID NO: 32) was designed in such a manner that it should hybridize to the nucleotide sequence encoding the $101^{st}$ position Ser to the $111^{th}$ position Ser of human κ chain constant region C terminus (SEQ ID NO: 24) and comprise the nucleotide sequence encoding restriction enzyme HindIII and NotI recognition sites and FLAG peptide (SEQ ID NO: 10), and two stop codons. By using these primers, $107^{th}$ amino acid residue of SEQ ID NO: 24, which is originally a cysteine residue, was replaced with a serine residue. PCR was conducted under the similar conditions to those of the above-mentioned manner using the two kinds of primers above-mentioned, and humanized PM1 antibody L chain expression vector RV1-PM1a (see WO92/19759) as the template DNA. The PCR product was purified using 1.5% low melting point agarose gel.

Next, the gene encoding humanized PM1 antibody single-chain Fv was amplified in the same manner. PCR was conducted under the same conditions as above-mentioned using EF1 (SEQ ID NO: 28) as the backward primer, SCP-K (SEQ ID NO: 33) as the forward primer, and pTMT-scFv as the template DNA. The forward primer SCP-K was designed in such a manner that it should hybridize to the nucleotide sequence encoding single-chain Fv C terminus shown in SEQ ID NO: 5, and comprise a nucleotide sequence that was complementary to the 5' end of the κ chain gene amplified by PCR. The PCR product was purified in the same manner.

Using the method shown in Example 2–3), the full-length cDNA fragment encoding shPM1Kappa was amplified. Namely, 100 ng each of the above-mentioned DNA fragments was assembled by primary PCR, and then 100 ng each of the backward primer EF-1 (SEQ ID NO: 28) and forward primer Kappa2 (SEQ ID NO: 32) was added to amplify the full-length cDNA fragment.

Figure 7:
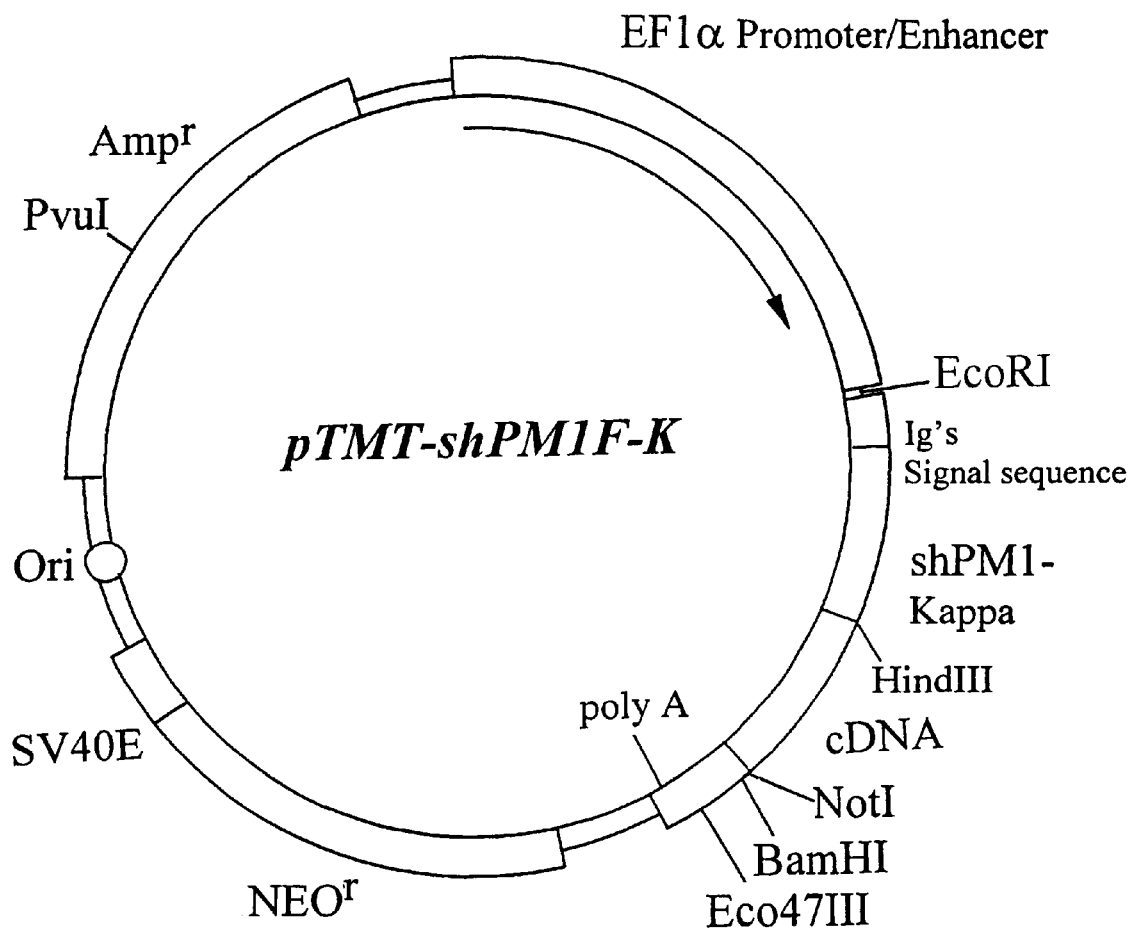
FIG. 7 schematically shows the structure of the expression vector pTMT-shPM1F-K. "shPM1Kappa" in the figure indicates a single-chain antibody. The other symbols are the same as FIG. 1 and FIG. 2.

After purifying the PCR product with 1.5% low melting point agarose gel, it was digested with restriction enzymes EcoRI and NotI, and inserted into pSFLAG vector to obtain shPM1Kappa expression vector pTMT-shPM1F-K (FIG. 7). Moreover, using the similar methods to those described in Example 5, a single-chain Fv having a bivalent variable region and shPM1Kappa-BvGS3 (SEQ ID NO: 34) expression vector pTMT-shPM1FK-BvGS3 were obtained.

4. Construction of the shPM1MCH4 Expression Vector

The gene encoding the fusion protein of humanized PM1 antibody single-chain Fv (SEQ ID NO: 23) and human μ chain constant region partial sequence (SEQ ID NO: 25) was constructed by PCR assembling. Namely, the genes encoding humanized PM1 antibody single-chain Fv and human t chain constant region partial sequence were amplified separately by PCR method, and were assembled by their complementarity. The full-length gene was then amplified by the external primer.

First, the gene encoding human μ chain constant region was amplified by PCR. The backward primer MCH4–1 (SEQ ID NO: 35) was designed in such a manner that it should hybridize to the nucleotide sequence encoding 5' end of human μ chain constant region exon 4 and comprise the nucleotide sequence of 3' end of humanized PM1 antibody single-chain Fv (SEQ ID NO: 23). The forward primer MCH4-2.1 (SEQ ID NO: 36) was designed in such a manner that it should hybridize to the nucleotide sequence encoding the extracellular region of human membrane-type μ chain constant region and comprise the restriction enzyme HindIII recognition site. PCR was conducted under the similar conditions to those of the above-mentioned manner using the two kinds of above-mentioned primers, and cDNA obtained from human myeloma cell-line CL-4 cells by common methods as the template DNA. The PCR product was purified using 1.5% low melting point agarose gel.

Next, the gene encoding humanized PM1 antibody single-chain Fv was amplified in the same manner. PCR was conducted under the same condition as mentioned above using EF1 (SEQ ID NO: 28) as the backward primer, SCP-Mu (SEQ ID NO: 37) as the forward primer, and pTMT-scFv as template DNA. The forward primer SCP-Mu was designed in such a manner that it should hybridize to the nucleotide sequence encoding single-chain Fv C terminus shown in SEQ ID NO: 23, and comprise a nucleotide sequence that was complementary to the 5' end of the μ chain partial sequence gene amplified by PCR. The PCR product was purified in the same manner.

Using the method shown in Example 2–3), the full-length cDNA fragment encoding shPM1MCH4 was amplified. Namely, 100 ng each of the above-mentioned DNA fragments were assembled by primary PCR, and then 100 pmol each of the backward primer EF-1 (SEQ ID NO: 28) and forward primer MCH4-2.2 (SEQ ID NO: 38) was added to amplify the full-length cDNA fragment. The forward primer MCH4-2.2 was designed in such a manner that it should hybridize to the 3' end of the nucleotide sequence encoding human membrane-type R chain partial sequence amplified above, and comprise the nucleotide sequence encoding FLAG peptide, two stop codons, and restriction enzyme NotI recognition site.

After purifying the PCR product with 1.5% low melting point agarose gel, it was digested with restriction enzymes EcoRI and NotI, and was inserted into pSFLAG vector to obtain shPM1-MCH4 expression vector pTMT-shPM1F-MCH4 (FIG. 7). Moreover, using methods as described in Example 5, single-chain Fv having a bivalent variable region, and shPM1-MCH4-BvGS3 (SEQ ID NO: 39) expression vector pTMT-shPM1FM-BvGS3 were obtained.

EXAMPLE 8

Screening of STX561 cDNA Library by the TMT Method Using the shPM1-kappa Expression Vector (FIG. 7)

1. Preparation of STX561 cDNA library mRNA from the mouse hematopoietic stromal cell line STX561 was prepared by the usual method and the cDNA synthesized from this was inserted into the TMT expression vector shPM1kappa to prepare STX561 cDNA library. cDNA library was prepared using cDNA synthesis kit (STRATAGENE, cDNA synthesis kit). Basically, the protocol of the cDNA synthesis kit of STRATAGENE was followed, with the modifications mentioned below. Namely, Superscript II of GIBCO-BRL was used as the reverse transcriptase, NotI-dT primer (Pharmacia Biotech, primer attached to 1st strand cDNA synthesis kit) as the primer for the first synthesis, HindIII-SmaI site adapter as the adapter added to the 5' terminus of cDNA, and Size sep 400 Spun Column of Pharmacia Biotech as the column for size fractionation.

Specifically, the cDNA library was prepared as follows: The starting material was 5 µg of mRNA, and first, a first strand was synthesized from 3' poly A tail by reverse transcriptase (Superscript II, GICO-BRL) using NotI-dT primer (Pharmacia Biotech, primer attached to 1st strand cDNA synthesis kit). Next, after synthesizing the second strand with DNA polymerase, both ends of the cDNA were blunt-ended, and the HindIII-SmaI site adaptor (Takara) was added. After digesting both ends with HindIII and NotI, size-fractionation (Pharmacia Biotech, Size sep 400 Spun Column) was done to remove cDNA fragments with 0.5 kb or less in size. The collected cDNA was inserted into the HindIII-NotI sites of TMT expression vector shPM1kappa, and the vectotr was introduced into *E. coli* DH10B (electroMAX DH10B, GIBCO-BRL) by electroporation method to prepare the STX561 cDNA library.

STX561 cDNA library was pooled by separating into 1000 clones/pool, and two pools thereof (pool no.: #kappa-1, #kappa-6), 2000 clones in total were used for screening by the TMT method.

2. Screening of STX cDNA Library by Panning

1) Transfection Into COS-7 Cells

2 µg each of the plasmid DNA prepared from #kappa-1 and #kappa-6 were transfected into COS-7 cells using FuGENE™6 (Boehringer-Mannheim).

Namely, COS-7 cells seeded in $1 \times 10^5$ cells/well (6-well plate) on the day prior to the transfection were cultured overnight under the conditions of 37° C. and 5% $CO_2$ in 2 ml of 10% fetal calf serum-containing DMEM culture medium (GIBCO-BRL). On the day of transfection, 6 µl FuGENE™ was added to 0.1 ml of serum-free DMEM culture medium and incubated for 5 min at room temperature, then mixed with 2 µg plasmid DNA, and incubated for further 15 min at room temperature. Next, this mixture was added to the above COS-7 cells, and incubated for 3 days under the conditions of 37° C. and 5% $CO_2$.

2) Preparation of the Panning Dish

A panning dish coated with goat anti-mouse IgG antibody (Dainippon Seiyaku, goat anti-mouse IgG (H+L chains)) was prepared according to the method of "Seed, B. et al., Proc. Natl. Acad. Sci. USA. (1987) 84, 3365–3369". Namely, goat anti-mouse IgG antibody was added to 50 mM Tris-HCl (pH9.5) to 10 µg/ml. The antibody solution thus prepared (3 ml) was added to 60 mm-diameter cell-culture dish, and incubated at room temperature for 3 hours. After washing three times with 0.15M NaCl solution, PBS containing 5% fetal calf serum, 1 mM EDTA, and 0.02% $NaN_3$ was added, and then, after blocking, the panning was done as follows.

3) Panning

COS-7 cells transfected as mentioned above, were detached from the plate with PBS containing 1 mM EDTA, washed once with PBS containing 5% fetal calf serum, suspended in 50 µl of FACS buffer (PBS containing 2% fetal calf serum and 0.05% $NaN_2$).

Soluble-type IL-6R (2 µg) was added to the cell-suspension and incubated for 90 min on ice. Next, after washed twice with FACS buffer, the cells were suspended in 50 µl of FACS buffer. Then, 1.5 µg of mouse anti-IL-6 receptor antibody MT-18 was added to the cell suspension, and the suspension was incubated for 30 min on ice. Cells were washed twice with FACS buffer, suspended in 2 ml of PBS containing 5% fetal calf serum and 0.02% $NaN_3$, and added to a panning plate coated with goat anti-mouse IgG antibody.

After incubating the above-mentioned various COS-7 cells on panning plates at room temperature for about 2 hours, the plates were gently washed three times with PBS containing 5% fetal calf serum and 0.02% $NaN_3$, and plasmid DNA were collected from cells bound to the panning dishes using Hirts' solution (solution containing 0.6% SDS and 10 mM EDTA). Half of the collected plasmid DNA were transfected into 40 µl of *E. coli* DH10B (electroMAX DH10B, GIBCO-BRL) by the electroporation method, and after incubating for 1 hr in 1 ml of SOC culture-medium, 50 µl was sampled for the titer-check and seeded onto an LB-ampicillin (100 µg/ml) plate. On the other hand, the remaining culture was transferred to 500 ml of LB-ampicillin (100 µg/ml) liquid culture medium and cultured. After an overnight culture, plasmid DNA were prepared by plasmid DNA purification kit (Plasmid-Maxi, QIAGEN) and cryopreserved at −20° C.

A 1 µg portion of each of the plasmid DNA obtained per pool was re-transfected into COS-7 cells using 3 µl of FuGENE™6 (Boehringer-Mannheim), and the second panning, and recovery and preparation of the plasmid DNA were done as mentioned above.

3. Analysis of the Nucleotide Sequence and Deduced Amino Acid Sequence of the Obtained cDNA Clone Following the first and second panning, colonies were randomly collected from the plates for titer checking, and after culturing each in 2 ml of LB-ampicillin (100 µg/ml) liquid culture medium, plasmid DNAs were prepared. Next, one more cDNA insert was screened by restriction enzyme analysis using SmaI and NotI, sequencing was done from the 5' side, and as a result of analyzing their nucleotide sequence and deduced amino acid sequence, it was revealed that genes of membrane-bound proteins could be selectively screened by using the TMT method. The results are shown in Table 1.

TABLE 1

| Pool name (1000 clones/pool) | Analyzed clone number | Clone number having transmembrane regions | Details (insert size, amino acid residue number, transmembrane region number) |
|---|---|---|---|
| First Panning | | | |
| kappa-1 | 11 | 1 | Cytochrome oxidase (0.75 kb, 44aa, 1TM) |
| kappa-6 | 7 | 3 | NADH-dehydrogenase (1.7 kb, 88aa, 2TM) NADH-dehydrogenase (1.7 kb, 88aa, 2TM) ATP-synthase (0.85 kb, 42aa, 1TM) |
| Second Panning | | | |
| kappa-1 | 11 | 4 | ATP-synthase (0.85 kb, 42aa, 1TM) ATP-synthase (0.85 kb, 42aa, 1TM) ATP-synthase (0.85 kb, 42aa, 1TM) Cytochrome oxidase 0.75 kb, 44aa, 1TM) |
| kappa-6 | 11 | 3 | NADH-dehydrogenase (1.2 kb, 81aa, 2TM) NADH-dehydrogenase (3.5 kb, 58aa, 2TM) Poly T (0.9 kb, 35aa, 1TM) |

From the first panning, known membrane-bound proteins, cytochrome oxidase (1 clone), NADH-dehydrogenase (2 clones), and ATP-synthase (1 clone) were obtained. On the other hand, from the second panning, known membrane-bound proteins, cytochrome oxidase (1 clone), NADH-dehydrogenase (2 clones), and ATP-synthase (3 clones) were obtained. All mentioned above are membrane-bound proteins localized in the mitochondria inner-membrane. For example, ATP-synthase is known to be one-transmembrane-type, cytochrome oxidase to be two-transmembrane-type, and NADH-dehydrogenase to be fifteen-transmembrane-type proteins. These results reveal that TMT method enables not only the isolation of type I membrane-bound proteins, but also proteins having multiple transmembrane regions.

A clone of poly T sequence obtained in the second panning is probably due to insertion of the cDNA comprising poly A in the opposite direction. Poly T is translated into an amino acid sequence in which phenylalanines, which are hydrophobic, are tandemly aligned, and is believed to have been isolated since it is extremely rich in hydrophobicity.

In addition, the percentage of membrane-bound proteins contained in the collected clones is higher in the second panning than in the first panning. This shows that membrane-bound proteins are selectively condensed by repeating pannings.

Thus, in an actual cDNA library screening system, the TMT method was revealed to be an effective method for selectively cloning type I membrane-bound proteins and membrane-bound proteins comprising multiple transmembrane regions.

Industrial Applicability

Due to structural problems, it is believed that antibody molecules cannot easily exert their antigen-binding activity when they are in states where they are accumulated on the cell membrane in the secreting process, and where they are agglutinated due to unnatural structures with fusion proteins and due to the amino acid composition. Therefore, as in the present invention, cells functionally expressing antibody fusion proteins on the cell-surface can be selectively screened by using a panning plate prepared using an antigen recognizing an antibody. Namely, the present invention provided a method of extremely selectively cloning genes encoding cell membrane-bound proteins, by effective removal of cells having fusion proteins with little or no antigen-binding activity on the cell surface.

What is claimed is:

1. A method for isolating or identifying a gene encoding a membrane-bound protein, the method comprising the steps of (i) introducing into cells a vector comprising a sequence comprising (a) a DNA encoding a secretable protein and (b) a cDNA ligated downstream of the secretable protein-encoding DNA, wherein the secretable protein can bind to an antigen and is selected from the group consisting of an antibody, a fragment of an antibody, and a single-chain antibody;

(ii) expressing in the cells a fusion protein encoded by the sequence comprising (a) and (b);

(iii) contacting the cells of (ii) with the antigen;

(iv) selecting a cell that binds to the antigen; and (v) isolating or identifying the cDNA comprised in the vector that was introduced into the selected cell.

2. The method of claim 1, further comprising determining the sequence of the cDNA isolated or identified in (v).

3. The method of claim 1, further comprising screening a cDNA library to obtain a full-length cDNA comprising the sequence of the cDNA isolated or identified in (v).

4. The method of claim 1, wherein the vector introduced into cells in step (i) is obtained by introducing a cDNA into a vector at a restriction enzyme site downstream of the 3' end of the secretable protein-encoding DNA.

5. The method of claim 1, wherein the vector introduced into cells in step (i) is obtained by introducing into a vector, a DNA comprising (a) a DNA encoding the secretable protein and (b) a cDNA ligated downstream of the 3' end of the secretable protein-encoding DNA.

6. The method of claim 1, wherein the DNA of (a) and the cDNA of (b) are ligated via a DNA encoding a peptide linker.

7. The method of claim 1, wherein the cDNA is derived from a cDNA library obtained from mammalian cells.

8. The method of claim 1, wherein the vector introduced into cells in step (i) comprises a DNA encoding a secretion signal sequence upstream of the 5' end of the DNA of (a).

9. The method of claim 1, wherein the secretable protein is an antibody.

10. The method of claim 1, wherein the secretable protein is a single-chain antibody.

11. The method of claim 10, wherein the vector contains a DNA encoding a constant region of an antibody ligated downstream of the 3' end of the DNA encoding the single-chain antibody.

12. The method of claim 1, wherein the antigen is bound to a support.

13. The method of claim 12, wherein the support is for cell-culturing.

* * * * *

UNITED STATES PATENT AND TRADEMARK OFFICE
CERTIFICATE OF CORRECTION

PATENT NO. : 6,610,485 B1
DATED : August 26, 2003
INVENTOR(S) : Masayuki Tsuchiya, Mikiyoshi Saito and Toshihiko Ohtomo It is certified that error appears in the above-identified patent and that said Letters Patent is hereby corrected as shown below:

Column 1,
Line 35, replace "upto" with -- up to --

Column 2,
Line 65, delete "." between "protein" and "having"

Column 3,
Line 1, delete "-" between "to" and "the"
Line 13, replace "3," with -- 3' --

Column 9,
Line 60, replace "ul" with -- $\mu$l --

Column 10,
Line 55, replace "ul" with -- $\mu$l --
Line 67, after "antibody" delete ";"

Column 11,
Line 24, replace "ul" with -- Tl --
Line 37, replace "PSFLAG" with -- pSFLAG --

Column 12,
Line 2, replace "Aportion" with -- A portion --
Line 32, replace "651th" with -- 651st --

Column 13,
Line 63, delete ":" after "DMEM"

Column 14,
Line 34, after "transfected" delete ":"
Line 35, replace "MM" with -- mM --

Column 17,
Line 6, replace "for30" with -- for 30 --

Column 19,
Lines 44, 53 and 56, replace "shPM1Kappa" with -- shPM1-Kappa --
Line 58, replace "shPM1CH4" with -- shPM1-MCH4 --
Line 63, replace "t" with -- $\mu$ --

UNITED STATES PATENT AND TRADEMARK OFFICE
CERTIFICATE OF CORRECTION

PATENT NO.    : 6,610,485 B1
DATED         : August 26, 2003
INVENTOR(S)   : Masayuki Tsuchiya, Mikiyoshi Saito and Toshihiko Ohtomo It is certified that error appears in the above-identified patent and that said Letters Patent is hereby corrected as shown below:

Column 20,
Line 31, replace "shPM1CH4" with -- shPM1-MCH4 --
Line 39, replace "R" with -- $\mu$ --

Column 21,
Line 17, replace "vectotr" with -- vector --

Signed and Sealed this

Eighteenth Day of January, 2005

JON W. DUDAS
*Director of the United States Patent and Trademark Office*